(12) United States Patent (10) Patent No.: US 9,289,140 B2
Ross et al. (45) Date of Patent: Mar. 22, 2016

(54) SYSTEMS AND METHODS FOR IMAGING CHANGES IN TISSUE

(75) Inventors: Brian D. Ross, Ann Arbor, MI (US); Alnawaz Rehemtulla, Plymouth, MI (US); Thomas Chenevert, Ann Arbor, MI (US); Charles R. Meyer, Ann Arbor, MI (US); Craig J. Galban, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1022 days.

(21) Appl. No.: 12/395,194

(22) Filed: Feb. 27, 2009

(65) Prior Publication Data

US 2009/0234237 A1 Sep. 17, 2009

Related U.S. Application Data

(60) Provisional application No. 61/032,825, filed on Feb. 29, 2008.

(51) Int. Cl.
*G01N 33/48* (2006.01)
*G01N 31/00* (2006.01)
*A61B 5/02* (2006.01)
*A61B 5/026* (2006.01)
(Continued)

(52) U.S. Cl.
CPC ............... *A61B 5/026* (2013.01); *A61B 5/415* (2013.01); *A61B 5/416* (2013.01); *A61B 6/507* (2013.01); *G06F 17/10* (2013.01); *G06F 17/11* (2013.01); *G06F 19/12* (2013.01); *G06F 19/24* (2013.01); *A61B 5/0263* (2013.01); *A61B 5/055* (2013.01); *A61B 6/501* (2013.01)

(58) Field of Classification Search
None
See application file for complete search history.

(56) References Cited

U.S. PATENT DOCUMENTS 6,163,152 A 12/2000 Bernstein et al.
6,381,296 B1 * 4/2002 Nishiura ........................ 378/4
(Continued)

FOREIGN PATENT DOCUMENTS

WO WO-01/56466 A2 8/2001
WO WO-02/061457 A2 8/2002
(Continued)

OTHER PUBLICATIONS

Magnetic Resonance Imaging, 2006, two pages. Churchill Livingstone's Dictionary of Nursing. Retrieved online on Nov. 10, 2011 <<http://www.credoreference.com/entry/ehscldictnursing/magnetic_resonance_imaging_mri>>.*

(Continued)

*Primary Examiner* — Russell S Negin
(74) *Attorney, Agent, or Firm* — Marshall, Gerstein & Borun LLP

(57) ABSTRACT

The present invention provides systems and methods for monitoring tissue regions. In particular, the present invention provides systems and methods for detecting changes in tissue regions over a period of time. In some embodiments, the systems and methods of the present invention are used to evaluate the effectiveness of a particular treatment of a tissue region. In some embodiments, the systems and methods of the present invention provide a parametric response map approach for detecting and analyzing changes in tissue regions over a period of time to detect and monitor disease or tissue health and to monitor the impact of therapeutic interventions.

19 Claims, 12 Drawing Sheets

(51) Int. Cl.
  G06F 19/12    (2011.01)
  G06F 19/24    (2011.01)
  G06F 17/10    (2006.01)
  G06F 17/11    (2006.01)
  A61B 5/00     (2006.01)
  A61B 5/055    (2006.01)
  A61B 6/00     (2006.01)

(56) References Cited

U.S. PATENT DOCUMENTS

| | | |
|---|---|---|
| 6,567,684 B1 | 5/2003 | Chenevert et al. |
| 6,579,240 B2 | 6/2003 | Bjaerum et al. |
| 6,845,342 B1 | 1/2005 | Basser et al. |
| 6,901,277 B2 | 5/2005 | Kaufman et al. |
| 6,969,991 B2 | 11/2005 | Bammer et al. |
| 7,078,897 B2 | 7/2006 | Yablonskiy et al. |
| 7,897,792 B2 | 3/2011 | Iikura et al. |
| 7,949,164 B2 | 5/2011 | Degani et al. |
| 8,185,186 B2 | 5/2012 | Ross et al. |
| 2003/0018245 A1* | 1/2003 | Kaufman et al. ............ 600/407 |
| 2003/0065260 A1 | 4/2003 | Cheng et al. |
| 2004/0254444 A1 | 12/2004 | Bittner |
| 2005/0105788 A1 | 5/2005 | Turek et al. |
| 2008/0021301 A1 | 1/2008 | Gonzalez et al. |
| 2009/0035218 A1 | 2/2009 | Ross et al. |
| 2009/0058417 A1 | 3/2009 | Yanasak et al. |
| 2009/0234237 A1 | 9/2009 | Ross et al. |
| 2010/0088339 A1 | 4/2010 | Rietzel et al. |
| 2010/0249099 A1 | 9/2010 | Rewcastle et al. |
| 2010/0254584 A1 | 10/2010 | Gulsun et al. |
| 2011/0009405 A1 | 1/2011 | Rewcastle et al. |
| 2011/0053907 A1 | 3/2011 | Rewcastle et al. |
| 2011/0066024 A1 | 3/2011 | Shih et al. |
| 2011/0077503 A1 | 3/2011 | Bonilha et al. |
| 2011/0187367 A1 | 8/2011 | Feiweier et al. |
| 2012/0316422 A1 | 12/2012 | Ross et al. |
| 2013/0004043 A1 | 1/2013 | Ross et al. |
| 2013/0004044 A1 | 1/2013 | Ross et al. |
| 2013/0129168 A1 | 5/2013 | Ross |

FOREIGN PATENT DOCUMENTS

| | | |
|---|---|---|
| WO | WO-2008/122056 A2 | 10/2008 |
| WO | WO-2008/154741 A1 | 12/2008 |
| WO | WO-2010/116124 A1 | 10/2010 |
| WO | WO-2011/137370 A2 | 11/2011 |
| WO | WO-2013/003826 A1 | 1/2013 |
| WO | WO-2013/006506 A1 | 1/2013 |
| WO | WO-2013/078370 A1 | 5/2013 |
| WO | WO-2013/166416 A1 | 11/2013 |

OTHER PUBLICATIONS

Proof of Jan. 1, 2007 date for [Kiessling et al., Current Medicinal Chemistry, 2007, vol. 14, pp. 77-91]; obtained on Nov. 10, 2011; one page.*

Besl, PJ, et al., "A Method for Registration of 3D Shapes" (1992) IEEE Trans. Pattern Analysis and Machine Intelligence 14(2):239-256.

Bookstein, FL "Principle Warps: Thin-Plate Splines and the Decomposition of Deformations" (1989) IEEE Transactions on Pattern Analysis and Machine Intelligence 11(6):567-585.

Breen, M, et al., "Three Dimensional Method for Comparing In Vivo Interventional MR Images of Thermally Ablated Tissue and Tissue Response" J Mag Res Imag 18:90-102, Jan. 2006.

Brix, G., et al. "Pharmacokinetic parameters in CNS Gd-DTPA enhanced MR imaging" J Comput Assist Tomogr 15, 621-628 (1991).

Brix, G. et al "Microcirculation and microvasculature in breast tumors: pharmacokinetic analysis of dynamic MR image series" Magn Reson Med 52, 420-429 (2004).

Cao, Y., et al. "Survival prediction in high-grade gliomas by MRI perfusion before and during early stage of RT" Int J Radiat Oncol Biol Phys 64, 876-885 (2006).

Chan, J.L., et al. "Survival and failure patterns of high-grade gliomas after three-dimensional conformal radiotherapy" J Clin Oncol 20, 1635-1642 (2002).

Collignon, A, et al., "3D Multi-Modality Medical Image Registration Using Feature Space Clustering" (1995) Lecture Notes in Computer Science 905: 195-204.

Degani, H., "Mapping pathophysiological features of breast tumors by MRI at high spatial resolution" Nat Med 3, 780-782 (1997).

Eyal, E. & Degani, H. NMR Biomed (2007), vol. 22, pp. 40-53.

Galbraith et al., "Reproducibility of dynamic contrast-enhanced MRI in human muscle and tumours: comparison of quantitative and semi-quantitative analysis." NMR Biomed 15, 132-142 (2002).

Hoffmann, U., "Pharmacokinetic mapping of the breast: a new method for dynamic MR mammography" Magn Reson Med 33, 506-514 (1995).

Hylton, N., "Dynamic contrast-enhanced magnetic resonance imaging as an imaging biomarker" (2006) J Clin Oncol 24, 3293-3298.

Jacobs, M, et al., "Registration and warping of magnetic resonance images to histological sections" (1999) Medical Physics 26(8):1568-1578.

Kiesling, F., et al., (2007) Curr Med Chem 14, 77-91, Jan. 1, 2007.

Kim, B, et al., "Mutual information for automated unwarping of rat brain autoradiographs" (1997) NeuroImage 5 (1):31-40.

Kim, et al., Proc. Intl. Soc. Mag. Reson. Med. 8 (2000) 1765.

Lazebnik, R, et al., "Volume Registratino Using Needle Paths and Point Landmarks for Evaluation of Interventional MRI Treatments" 2003 IEEE Trans Med Imaging 22(5):653-660.

Lee et al., "A feasibility study evaluating the functional diffusion map as a predictive imaging biomarker for detection of treatment response in a patient with metastatic prostate cancer to the bone" Neoplasia, 9(12):1003-1011 (2007).

Meyer CR, et al., "Demonstration of accuracy and clinical versatility of mutual information for automatic multimodality image fusion using affine and thin-plate spline warped geometric deformations" Med Image Anal. 1997;1:195-206.

Meyer, CR, "A Methodology for Registration of a Histological Slide and MRI Volume Based on Optimizing Mutual Information" (2006) Molecular Imaging 5(1):16-23.

O'Connor, J.P., et al., "DCE-MRI biomarkers in the clinical evaluation of antiangiogenic and vascular disrupting agents" Br J Cancer 96, 189-195 (2007), Jan. 9, 2007.

Ostergaard, L., et al., "High resolution measurement of cerebral blood flow using intravascular tracer bolus passages. Part I: Mathematical approach and statistical analysis" Magn Reson Med 36, 715-725 (1996).

Park, H, et al., M Piert, A Kahn, R Shah, H Hussain, J Siddiqui, C Meyer (2008) Registration methodology for histological sections and ex vivo imaging of human prostate, Academic Radiology (accepted for publication).

Pelizarri, CA, et al., "Three Dimensional Correlation of Pet, CT and MRI Images" (1987) J. Nucl. Med. 28(4):683.

Rosen, et al., "Perfusion imaging with NMR contrast agents" Magn Reson Med 14, 249-265 (1990).

Thomas, A.L., et al. "Phase I study of the safety, tolerability, pharmacokinetics, and pharmacodynamics of PTK787/ZK 222584 administered twice daily in patients with advanced cancer" J Clin Oncol 23, 4162-4171 (2005).

Tofts, P.S. "Modeling tracer kinetics in dynamic Gd-DTPA MR imaging" (1997) J Magn Reson Imaging 7, 91-101.

Tofts, P.S., et al. "Estimating kinetic parameters from dynamic contrast-enhanced T(1)-weighted MRI of a diffusable tracer: standardized quantities and symbols" (1999) J Magn Reson Imaging 10, 223-232.

Viola, P, et al., (1995) "Alignment by maximization of mutual information" Proceedings of 5th Int'l. Conf. on Computer Vision, MIT, IEEE Press 95CH35744: 16-23.

Wilson, D, et al., (2004) M Breen, R Lazebnik, S Nour, J Lewin (2004) Radiofrequency thermal ablation: 3D MR histology correlation for localization of cell death in MR lesion images, in Proceedings of Internat Symp Biomed Imaging, Arlington, VA: 1537-1540.

(56) References Cited

OTHER PUBLICATIONS

Xiong, H.Q., et al. "A phase I surrogate endpoint study of SU6668 in patients with solid tumors" Invest New Drugs 22, 459-466 (2004).
Zahra, M.A., et al., "Dynamic contrast-enhanced MRI as a predictor of tumour response to radiotherapy" Lancet Oncol 8, 63-74 (2007).
Zarow, C, et al., "A Standardized Method for rain-Cutting Suitable for Both Stereology and MRI-Brain Co-Registration" 2004 J Neuorsci Methods 139:209-215.
Bagrodia et al., Mechanisms of intrinsic and acquired resistance to kinase-targeted therapies, Pigment Cell Melanoma Res., 25(6):819-31 (2012).
Baines et al., Inhibition of Ras for cancer treatment: the search continues, Future Med. Chem., 3(14):1787-808 (2011).
Bammer et al., Analysis and generalized correction of the effect of spatial gradient field distortions in diffusion weighted imaging, Magn. Res. Med, 50:560-9 (2003).
Bammer et al., Assessment of spatial gradient field distortion in diffusion-weighted imaging, ISMRM Proceedings (2002).
Besil et al., A method for registration of 3-D shapes, IEEE Trans. Pattern Analysis and Machine Intelligence, 14(2):239-56 (1992).
Bing et al., Voxel-by-voxel functional diffusion mapping for early evaluation of breast cancer treatment, Information Processing in Medical Imaging, pp. 276-287 (2009).
Bookstein et al., Principal Warps: Thin-plate splines and the decomposition of deformations, IEEE Transactions on Pattern Analysis and Machine Intelligence, 11(6):567-85 (1989).
Breen et al., Three-dimensional method for comparing in vivo interventional MR images of thermally ablated tissue with tissue response, J. Magn. Reson. Imaging, 18(1):90-102 (2003).
Brix et al., Microcirculation and microvasculature in breast tumors: pharmacokinetics analysis of dynamic MR image series, Mag. Reson. Med., 52:420-9 (2004).
Brix et al., Pharmacokinetic parameters in CNS Gd-DTPA enhanced MR imaging, J. Comput Assist. Tomogr., 15:621-8 (1991).
Bubley et al., Eligibility and response guidelines for phase II clinical trials in androgen-independent prostate cancer: recommendations from the Prostate-Specific Antigen Working Group, J. Clin. Oncol., 17(11):3461-7 (1999).
Bulinski et al., Overexpression of MAP4 inhibits organelle motility and trafficking in vivo, J. Cell Sci., 110(Pt. 4):3055-64 (1997).
Cao et al., Survival prediction in high-grade gliomas by MRI perfusion before and during early stage of RT, Int. J. Radiat. Oncol. Biol. Phys., 64:876-85 (2006).
Carracedo et al., Inhibition of mTORC1 leads to MAPK pathway activation through a PI3K-dependent feedback loop in human cancer, J. Clin Invest., 118(9):3065-74 (2008).
Castellano et al., RAS Interaction with PI3K: More Than Just Another Effector Pathway, Genes Cancer, 2(3):261-74 (2011).
Chan et al., Survival and failure patterns of high-grade gliomas after three-dimensional conformal radiotherapy, J. Clin. Oncol., 20:1635-42 (2002).
Chenevert et al., Diffusion coefficient measurement using a temperature-controlled fluid for quality control in multicenter studies, J. Magn. Reson. Imaging, 34(4):983-7 (2011).
Chenevert et al., Diffusion magnetic resonance imaging: an early surrogate marker of therapeutic efficacy in brain tumors, J. Natl. Cancer Inst., 92(24):2029-36 (2000).
Chenevert et al., Diffusion MRI: a new strategy for assessment of cancer therapeutic efficacy, Mol. Imaging, 1(4):336-43 (2002).
Chenevert et al., Icewater for quality control of diffusion measurements in multi-center trials, in Proceedings of the 19th Annual Meeting of ISMRM, Montreal, Quebec, Canada, p. 912 (2011).
Chenevert et al., Monitoring early response of experimental brain tumors to therapy using diffusion magnetic resonance imaging, Clin. Cancer Res., 3(9):1457-66 (1997).
Collignon et al., 3D multi-modality medical image registration using feature space clustering, Lecture Notes in Computer Science, 905:195-204 (1995).
Degani, Mapping pathophysiological features of breast tumors by MRI at high spatial resolution, Nat. Med., 3:780-2 (1997).

Early Breast Cancer Trialists Collaborative Group, Polychemotherapy for early breast cancer: an overview of the randomised trials, The Lancet, 352:930-42 (1998).
Eda et al., The relations between expiratory chest CT using helical CT and pulmonary function tests in emphysema, Am. J. Respir. Crit Care Med., 155(4):1290-4 (1997).
Ellingson et al., Volumetric analysis of functional diffusion maps is a predictive imaging biomarker for cytotoxic and anti-angiogenic treatments in malignant gliomas, J. Neuro-Oncol., 102(1):95-103 (2010).
Engelman et al., Effective use of PI3K and MEK inhibitors to treat mutant Kras G12D and PIK3CA H1047R murine lung cancers, Nat. Med., 14(12):1351-6 (2008).
Evelhoch et al., Applications of magnetic resonance in model systems: cancer therapeutics, Neoplasia, 2(1-2):152-65 (2000).
Eyal et al., NMR Biomed., 22:40-53 (2007).
Falchook et al., Activity of the oral MEK inhibitor trametinib in patients with advanced melanoma: a phase 1 dose-escalation trial, Lancet Oncol., 13(8):782-9 (2012).
Fogelman et al., Positron emission tomography and bone metastases, Semin. Nucl. Med., 35(2):135-42 (2005).
Galban et al., A feasibility study of parametric response map analysis of diffusion-weighted magnetic resonance imaging scans of head and neck cancer patients for providing early detection of therapeutic efficacy, Translational Oncol., 2:184-90 (2009).
Galban et al., Prospective analysis of parametric response map-derived MRI biomarkers: identification of early and distinct glioma response patterns not predicted by standard radiographic assessment, Clin. Cancer Res., 17(14):4751-60 (2011).
Galbraith et al., Reproducibility of dynamic contrast-enhanced MRI in human muscle and tumours: comparison of quantitative and semi-quantitative analysis, NMR Biomed., 15:132-42 (2002).
Galons et al., Early increases in breast tumor xenograft water mobility in response to paclitaxel therapy detected by non-invasive diffusion magnetic resonance imaging, Neoplasia, 1(2):113-7 (1999).
Gevenois et al., Comparison of computed density and macroscopic morphometry in pulmonary emphysema, Am. J. Respir. Crit. Care Med., 152(2):653-7 (1995).
Gevenois et al., Comparison of computed density and microscopic morphometry in pulmonary emphysema, Am. J. Respir. Crit. Care Med., 154(1):187-92 (1996).
Gorbunova et al., Early detection of emphysema progression, Med. Image Comput. Comput. Assist. Interv., 13(Pt. 2):193-200 (2010).
Gorbunova et al., Weight preserving image registration for monitoring disease progression in lung CT, Medical Image Computing and Computer-Assisted Intervention A MICCAI 2008, pp. 863-870 (2008).
Green et al., Multi-scale rigid registration to detect damage in micro-CT images of progressively loaded bones, 2011 8th IEEE International Symposium on Biomedical Imaging: From Nano to Micro, IEEE, pp. 1231-1234 (2011).
Hall et al., Therapeutic efficacy of DTI-015 using diffusion magnetic resonance imaging as an early surrogate marker, Clin. Cancer Res., 10(23):7852-9 (2004).
Hamaoka et al., Bone imaging in metastatic breast cancer, J. Clin. Oncol., 22(14):2942-53 (2004).
Hamstra et al., Evaluation of the functional diffusion map as an early biomarker of time-to-progression and overall survival in high-grade glioma, Proc. Natl. Acad. Sci. USA, 102(46):16759-64 (2005).
Hamstra et al., Functional diffusion map as an early imaging biomarker for high-grade glioma: correlation with conventional radiologic response and overall survival, J. Clin. Oncol., 26(20):3387-94 (2008).
Hamstra et al., The use of 19F spectroscopy and diffusion-weighted MRI to evaluate differences in gene-dependent enzyme prodrug therapies, Mol. Ther., 10(5):916-28 (2004).
Hatzivassiliou et al., RAF inhibitors prime wild-type RAF to activate the MAPK pathway and enhance growth, Nature, 464(7287):431-5 (2010).
Hayward et al., Assessment of response to therapy in advanced breast cancer (an amendment), Br. J. Cancer, 38(1):201 (1978).
Hayward et al., Assessment of response to therapy in advanced breast cancer, Br. J. Cancer, 35(3):292-8 (1977).

(56) References Cited

OTHER PUBLICATIONS

Helen et al., Segmentation of pulmonary parenchyma in CT lung images based on 2D Otsu optimized by PSO, Emerging Trends in Electrical and Computer Technology, 2011 International Conference on IEEE, pp. 536-541 (2011).
Hoffmann, Pharmacokinetic mapping of the breast: a new method for dynamic MR mammography, Magn. Reson. Med., 33:506-14 (1995).
Hogg et al., The nature of small-airway obstruction in chronic obstructive pulmonary disease, N. Engl. J. Med., 350(26):2645-53 (2004).
Hu et al., Automatic lung segmentation for accurate quantitation of volumetric X-ray CT images, IEEE Trans. Med. Imaging, 20(6):490-8 (2001).
Hylton, Dynamic contrast-enhanced magnetic resonance imaging as an imaging biomarker, J. Clin. Oncol., 24:3293-8 (2006).
Infante et al., Safety, pharmacokinetic, pharmacodynamic, and efficacy data for the oral MEK inhibitor trametinib: a phase 1 dose-escalation trial, Lancet Oncol., 13(8):773-81 (2012).
International Search Report and Written Opinion, PCT/US2012/066338, mailing date Mar. 11, 2013.
Jacobs et al., Registration and warping of magnetic resonance images to histological sections, Med. Phys., 26(8):1568-78 (1999).
Janke et al., Use of spherical harmonic deconvolution methods to compensate for nonlinear gradient effects on MRI images, Magn. Reson. Med., 52(1):115-22 (2004).
Jemal et al., Cancer statistics, 2010, CA Cancer J. Clin., 60(5):277-300 (2010).
Jennings et al., Early response of prostate carcinoma xenografts to docetaxel chemotherapy monitored with diffusion MRI, Neoplasia, 4(3):255-62 (2002).
Jordan et al., Dynamic contrast-enhanced and diffusion MRI show rapid and dramatic changes in tumor microenvironment in response to inhibition of HIF-1alpha using PX-478, Neoplasia, 7(5):475-85 (2005).
Kalikin et al., In vivo visualization of metastatic prostate cancer and quantitation of disease progression in immunocompromised mice, Cancer Biol. Ther., 2(6):656-60 (2003).
Karreth et al., C-Raf inhibits MAPK activation and transformation by B-Raf(V600E), Mol. Cell, 36(3):477-86 (2009).
Kiesling et al., Curr. Med. Chem., 14:77-91 (2007).
Kim et al., Correction of local deformations in fMRI by 3D non-linear warping in map-slice-to-volume approach, Proc. Intl. Soc. Mag. Reson. Med., 8:1765 (2000).
Kim et al., CT metrics of airway disease and emphysema in severe COPD, Chest., 136(2):396-404 (2009).
Kim et al., Mutual information for automated unwarping of rat brain autoradiographs, Neuroimage, 5(1):31-40 (1997).
Kim et al., Phase II study of the MEK1/MEK2 inhibitor Trametinib in patients with metastatic BRAF-mutant cutaneous melanoma previously treated with or without a BRAF inhibitor, J. Clin. Oncol., 31(4):482-9 (2013).
Kubo et al., Expiratory and inspiratory chest computed tomography and pulmonary function tests in cigarette smokers, Eur. Respir. J., 13(2):252-6 (1999).
Latour et al., Time-dependent diffusion of water in a biological model system, Proc. Natl. Acad. Sci. USA, 91(4):1229-33 (1994).
Laun et al., How background noise shifts eigenvectors and increases eigenvalues in DTI, MAGMA, 22(3):151-8 (2009).
Lazebnik et al., Volume registration using needle paths and point landmarks for evaluation of interventional MRI treatments, IEEE Trans. Med. Imaging, 22(5):653-60 (2003).
Lee et al., A feasibility study evaluating the functional diffusion map as a predictive imaging biomarker for detection of treatment response in a patient with metastic prostate cancer to the bone, Neoplasia, 9(12):1003-11 (2007).
Lee et al., Dynamic imaging of emerging resistance during cancer therapy, Cancer Res., 66(9):4687-92 (2006).
Lee et al., Prospective early response imaging biomarker for neoadjuvant breast cancer chemotherapy, Clin. Cancer Res., 13(2 Pt. 1):443-50 (2007).
Leung et al., Automatic quantification of changes in bone in serial MR images of joints, IEEE Transactions on Medical Imaging, 25(12):1617-26 (2006).
Li et al., Pulmonary CT image registration and warping for tracking tissue deformation during the respiratory cycle through 3D consistent image registration, Med. Phys., 35(12):5575-83 (2008).
Lorusso et al., Phase I and pharmacodynamic study of the oral MEK inhibitor CI-1040 in patients with advanced malignancies, J. Clin. Oncol., 23(23):5281-93 (2005).
Low et al., Novel breathing motion model for radiotherapy, Int. J. Radiat. Oncol. Biol. Phys., 63(3):921-9 (2005).
Lyng et al., Measurement of cell density and necrotic fraction in human melanoma xenografts by diffusion weighted magnetic resonance imaging, Magn. Reson. Med., 43(6):828-36 (2000).
Ma et al., Tetrahedron: asymmetry, 8(6):883-8 (1997).
Ma et al., Voxel-by-voxel functional diffusion mapping for early evaluation of breast cancer treatment, Inf. Process. Med. Imaging, 21:276-87 (2009).
Macdonald et al., Response criteria for phase II studies of supratentorial malignant glioma, J. Clin. Oncol., 8(7):1277-80 (1990).
Magnetic Resonance Imaging, two pages, Churchill Livingstone's Dictionary of Nursing (2006).
Matsuoka et al., Quantitative assessment of air trapping in chronic obstructive pulmonary disease using inspiratory and expiratory volumetric MDCT, AJR Am. J. Roentgenol., 190(3):762-9 (2008).
Matsuoka et al., Quantitative assessment of peripheral airway obstruction on paired expiratory/inspiratory thin-section computed tomography in chronic obstructive pulmonary disease with emphysema, J. Comput. Assist. Tomogr., 31(3):384-9 (2007).
Mattiello et al., The b matrix in diffusion tensor echo-planar imaging, Magn. Reson. Med., 37(2):292-300 (1997).
McCubrey et al., Emerging Raf inhibitors, Expert Opin. Emerg. Drugs, 14(4):633-48 (2009).
Mehta et al., Monitoring radiographic brain tumor progression, Toxins (Basel), 3(3):191-200 (2011).
Meyer et al., A methodology for registration of a histological slide and in vivo MRI volume based on optimizing mutual information, Mol. Imaging, 5(1):16-23 (2006).
Meyer et al., Demonstration of accuracy and clinical versatility of mutual information for automatic multimodality image fusion using affine and thin-plate spline warped geometric deformations, Med. Image Anal., 1(3):195-206 (1997).
Mirzoeva et al., Basal subtype and MAPK/ERK kinase (MEK)-phosphoinositide 3-kinase feedback signaling determine susceptibility of breast cancer cells to MEK inhibition, Cancer Res., 69(2):565-72 (2009).
Moffat et al., Diffusion imaging for evaluation of tumor therapies in preclinical animal models, MAGMA, 17(3-6):249-59 (2004).
Moffat et al., Diffusion MR imaging in adult neoplasia, CUP, Cambridge: Physiological MR in Clinical Neuroscience, (2004).
Moffat et al., Functional diffusion map: a noninvasive MRI biomarker for early stratification of clinical brain tumor response, Proc. Natl. Acad. Sci. USA, 102(15):5524-9 (2005).
Moffat et al., The functional diffusion map: an imaging biomarker for the early prediction of cancer treatment outcome, Neoplasia, 8(4):259-67 (2006).
Montagut et al., Targeting the RAF-MEK-ERK pathway in cancer therapy, Cancer Lett., 283(2):125-34 (2009).
Muhlradt et al., Epothilone B stabilizes microtubuli of macrophages like taxol without showing taxol-like endotoxin activity, Cancer Res., 57(16):3344-6 (1997).
Nakano et al., Computed tomographic measurements of airway dimensions and emphysema in smokers. Correlation with lung function, Am. J. Respir. Crit. Care Med., 162(3 Pt. 1):1102-8 (2000).
Nicolaou et al., Synthesis of epothilones A and B in solid and solution phase, Nature, 387(6630):268-72 (1997).
O'Connor et al., DCE-MRI biomarkers in the clinical evaluation of antiangiogenic and vascular disrupting agents, Br. J. Cancer, 96:189-95 (2007).
Ostergard et al., High resolution measurement of cerebral blood flow using intravascular tracer bolus passages, Part I: Mathematical approach and statistical analysis, Magn. Reson. Med., 36:715-25 (1996).

(56) References Cited

OTHER PUBLICATIONS

Ozcan et al., Characterization of imaging gradients in diffusion tensor imaging, J. Magn. Reson., 207(1):24-33 (2010).

Padhani et al., Diffusion-weighted magnetic resonance imaging as a cancer biomarker: consensus and recommendations, Neoplasia, 11(2):102-25 (2009).

Panda et al., Differential effects of vinblastine on polymerization and dynamics at opposite microtubule ends, J. Biol. Chem., 271(47):29807-12 (1996).

Panda et al., Stabilization of microtubule dynamics by estramustine by binding to a novel site in tubulin: a possible mechanistic basis for its antitumor action, Proc. Natl. Acad. Sci. USA, 94(20):10560-4 (1997).

Park et al., Registration methodology for histological sections and ex vivo imaging of human prostate, Academic Radiology, 15(8) (Aug. 2008).

Pelizzari et al., Three dimensional correlation of PET, CT and MRI images, J. Nucl. Med., 28(4):682-3 (1987).

Petrylak et al., Docetaxel and estramustine compared with mitoxantrone and prednisone for advanced refractory prostate cancer, N. Engl. J. Med., 351(15):1513-20 (2004).

Poulikakos et al., RAF inhibitors transactivate RAF dimers and ERK signalling in cells with wild-type BRAF, Nature, 464(7287):427-30 (2010).

Preusser et al., Current concepts and management of glioblastoma, Ann. Neurol., 70(1):9-21 (2011).

Regan et al., Genetic epidemiology of COPD (COPDGene) study design, COPD, 7(1):32-43 (2010).

Rehemtulla et al., Molecular imaging of gene expression and efficacy following adenoviral-mediated brain tumor gene therapy, Mol. Imaging, 1(1):43-55 (2002).

Reinhardt et al., Registration-based estimates of local lung tissue expansion compared to xenon CT measures of specific ventilation, Med. Image Anal., 12(6):752-63 (2008).

Reinhardt et al., Registration-derived estimates of local lung expansion as surrogates for regional ventilation, Int. Process. Med. Imaging, 20:763-74 (2007).

Reischauer et al., Bone metastases from prostate cancer: assessing treatment response by using diffusion-weighted imaging and functional diffusion maps—initial observations, Radiology, 257(2):523-31 (2010).

Robson, Non-linear gradients on clinical MRI systems introduce systematic errors in ADC and DTI measurements, ISMRM Proceedings (2002).

Rodrigues et al., The C-neu mammary carcinoma in Oncomice; characterization and monitoring response to treatment with herceptin by magnetic resonance methods, MAGMA, 17(3-6):260-70 (2004).

Romeo et al., Magnet field profiling: analysis and correcting coil design, Magn. Reson. Med., 1(1):44-65 (1984).

Rosen et al., Perfusion imaging with NMR contrast agents, Magn. Reson. Med., 14:249-65 (1990).

Ross et al. Assessment of the functional diffusion map: an imaging biomarker for early stratification of glioma clinical response, 2006 ASCO Annual Meeting Journal of Clinical Oncology, 24(18s): 1518 (2006).

Ross et al., Contributions of cell kill and posttreatment tumor growth rates to the repopulation of intracerebral 9L tumors after chemotherapy: an MRI study, Proc. Natl. Acad. Sci. USA, 95(12):7012-7 (1998).

Ross et al., Evaluation of cancer therapy using diffusion magnetic resonance imaging, Mol. Cancer Ther., 2(6):581-7 (2003).

Ross et al., Magnetic resonance imaging in cancer research, Eur. J. Cancer, 38(16):2147-56 (2002).

Ross et al., The role of magnetic resonance in the evaluation of cancer therapeutics, Clin. Cancer Res., 5:3870s-1s (1999).

Roth et al., High-b-value diffusion-weighted MR imaging for pretreatment prediction and early monitoring of tumor response to therapy in mice, Radiology, 232(3):685-92 (2004).

Sawyers, Imatinib GIST keeps finding new indications: successful treatment of dermatofibrosarcoma protuberans by targeted inhibition of the platelet-derived growth factor receptor, J. Clin. Oncol., 20(17):3568-9 (2002).

Schepkin et al., Proton and sodium MRI assessment of emerging tumor chemotherapeutic resistance, NMR Biomed., 19(8):1035-42 (2006).

Scher et al., Prostate cancer clinical trial end points: "RESIST" ing a step backwards, Clin. Cancer Res., 11(14):5223-32 (2005).

Scher et al., The association between measures of progression and survival in castrate-metastatic prostate cancer, Clin. Cancer Res., 13(5):1488-92 (2007).

Sebolt-Leopold et al., Targeting the mitogen-activated protein kinase cascade to treat cancer, Nat. Rev. Cancer, 4(12):937-47 (2004).

Sebolt-Leopold, Advances in the development of cancer therapeutics directed against the RAS-mitogen-activated protein kinase pathway, Clin. Cancer Res., 14(12):3651-6 (2008).

Shimizu et al., The clinical effect of the dual-targeting strategy involving PI3K/AKT/mTOR and RAS/MEK/ERK pathways in patients with advanced cancer, Clin. Cancer Res., 18(8):2316-25 (2012).

Sos et al., Identifying genotype-dependent efficacy of single and combined PI3K- and MAPK-pathway inhibition in cancer, Proc. Natl. Acad. Sci. USA, 106(43):18351-6 (2009).

Stegman et al., Diffusion MRI detects early events in the response of a glioma model to the yeast cytosine deaminase gene therapy strategy, Gene Ther., 7(12):1005-10 (2000).

Taichman et al., The evolving biology and treatment of prostate cancer, J. Clin. Invest., 117(9):2351-61 (2007).

Tannock et al., Docetaxel plus prednisone or mitoxantrone plus prednisone for advanced prostate cancer, N. Engl. J. Med., 351(15):1502-12 (2004).

Therasse et al., New guidelines to evaluate the response to treatment in solid tumors. European Organization for Research and Treatment of Cancer, National Cancer Institute of the United States, National Cancer Institute of Canada, J. Natl. Cancer Inst., 92(3):205-16 (2000).

Thomas et al., Phase I study of the safety, tolerability, pharmacokinetics and pharmacodynamics of PTK787/ZK 222584 administered twice daily in patients with advanced cancer, J. Clin. Oncol., 23:4162-71 (2005).

Tofts et al., Estimating kinetic parameters from dynamic contrast-enhanced T(1)-weighted MRI of a diffusable tracer: standardized quantities and symbols, J. Magn. Reson. Imaging, 10:223-32 (1999).

Tofts, Modeling tracer kinetics in dynamic Gd-DTPA MR imaging, J. Magn. Reson. Imaging, 7:91-101 (1997).

Vasquez et al., Nanomolar concentrations of nocodazole alter microtubule dynamic instability in vivo and in vitro, Mol. Biol. Cell, 8(6):973-85 (1997).

Viola et al., Alignment by maximization of mutual information, in Proceedings of 5th Intl. Conf. on Computer Vision, MIT, IEEE Press 95CH35744:16-23 (1995).

Washko et al., Identification of early interstitial lung disease in smokers from the COPDGene Study, Acad. Radiol., 17(1):48-53 (2010).

Washko et al., Lung volumes and emphysema in smokers with interstitial lung abnormalities, N. Engl. J. Med., 364(10):897-906 (2011).

Watts et al., "Relationship Between Changes in BMD and Nonvertebral Fracture Incidence Associated with Risedronate: Reduction in risk of Nonvertebral Fracture is not Related to Change in BMD," J Bone Miner Res. 20:2097-104 (2005).

Wee et al., PI3K pathway activation mediates resistance to MEK inhibitors in KRAS mutant cancers, Cancer Res., 69(10):4286-93 (2009).

Wen et al., Updated response assessment criteria for high-grade gliomas: response assessment in neuro-oncology working group, J. Clin. Oncol., 28(11):1963-72 (2010).

Wilson et al., Radiofrequency thermal ablation: 3D MR histology correlation for localization of cell death in MR lesion images, in: Proceedings of Intl. Symp. Biomed. Imaging, pp. 1537-1540 (2004).

World Health Organization, WHO Handbook for Reporting Results of Cancer Treatment, World Health Organization Offset Publication, Atlanta (1979).

(56) References Cited

OTHER PUBLICATIONS

Wu et al., A method for calibrating diffusion gradients in diffusion tensor imaging, J. Comput. Assist. Tomogr., 31(6):984-93 (2007).

Xiong et al., A phase I surrogate endpoint study of SU68868 in patients with solid tumors, Invest. New Drugs, 22:459-66 (2004).

Yamashiro et al., Collapsibility of lung volume by paired inspiratory and expiratory CT scans: correlations with lung function and mean lung density, Acad. Radiol., 17(4):489-95 (2010).

Yim et al., Deformable lung registration between exhale and inhale CT scans using active cells in a combined gradient force approach, Med. Phys., 37(8):4307-17 (2010).

Yin et al., Mass preserving nonrigid registration of CT lung images using cubic B-spline, Med. Phys., 36(9):4213-22 (2009).

Yu et al., Response and determinants of cancer cell susceptibility to PI3K inhibitors: combined targeting of PI3K and Mek1 as an effective anticancer strategy, Cancer Biol. Ther., 7(2):307-15 (2008).

Zahra et al., Dynamic contrast-enhanced MRI as a predictor of tumour response to radiotherapy, Lancet Oncol., 8:63-74 (2007).

Zarow et al., A standardized method for brain-cutting suitable for both stereology and MRI-brain brain co-registration, J. Neurosci. Methods, 139(2):209-15 (2004).

C158 Zhao et al., Early detection of treatment response by diffusion-weighted 1H-NMR spectroscopy in a murine tumour in vivo, Br. J. Cancer, 73(1):61-4 (1996).

Dhermain et al., Advanced MRI and PET imaging for assessment of treatment response in patients with gliomas, The Lancet Neurology, 9(9):906-20 (2010).

Galban et al., The parametric response map is an imaging biomarker for early cancer treatment outcome, Nature Medicine, 15(5):572-6 (2009).

Sawllani et al., Glioblastoma: a method for predicting response to antiangiogenic chemotherapy by using MR perfusion imaging-pilot study, Radiology, 255(2):622 (2010).

Tsien et al., Parametric response map as an imaging biomarker to distinguish progression from pseudoprogression in high-grade glioma, J. Clin. Oncol., 28(13):2293-9 (2010).

Vilanova et al., Diffusion-weighted whole-body MR screening, Eur. J. Radiology, 67(3):440-7 (2008).

Zacharaki et al., Orbit: A multiresolution framework for deformable registration of brain tumor images, IEEE Trans. Med. Imaging, 27(8):1003-17 (2008).

\* cited by examiner

WEEK 1

WEEK 3

SYSTEMS AND METHODS FOR IMAGING CHANGES IN TISSUE

CROSS REFERENCE TO RELATED APPLICATIONS

The present application claims priority to U.S. Provisional Patent Application No. 61/032,825, filed Feb. 29, 2008, hereby incorporated by reference in its entirety.

STATEMENT REGARDING FEDERALLY SPONSORED RESEARCH OR DEVELOPMENT

This invention was made with government support under Grant Nos. CA085878, CA083099, CA093990, and CA087634 awarded by the National Institutes of Health. The government has certain rights in the invention.

FIELD OF THE INVENTION

The present invention provides systems and methods for monitoring tissue regions. In particular, the present invention provides systems and methods for detecting changes in tissue regions over a period of time. In some embodiments, the systems and methods of the present invention are used to evaluate the effectiveness of a particular treatment of a tissue region. In some embodiments, the systems and methods of the present invention provide a parametric response map approach for detecting and analyzing changes in tissue regions over a period of time to detect and monitor disease or tissue health and to monitor the impact of therapeutic interventions.

BACKGROUND

Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer may affect people at all ages, but risk tends to increase with age. It is one of the principal causes of death in developed countries.

There are many types of cancer. Severity of symptoms depends on the site and character of the malignancy and whether there is metastasis. A definitive diagnosis usually requires the histologic examination of tissue by a pathologist. This tissue is obtained by biopsy or surgery. Most cancers can be treated and some cured, depending on the specific type, location, and stage. Once diagnosed, cancer is usually treated with a combination of surgery, chemotherapy and radiotherapy. As research develops, treatments are becoming more specific for the type of cancer pathology. Drugs that target specific cancers already exist for several types of cancer. If untreated, cancers may eventually cause illness and death, though this is not always the case.

Cancer can be treated by surgery, chemotherapy, radiation therapy, immunotherapy, monoclonal antibody therapy or other methods. The choice of therapy depends upon the location and grade of the tumor and the stage of the disease, as well as the general state of the patient (performance status). A large number of experimental cancer treatments are also under development.

Complete removal of the cancer without damage to the rest of the body is the goal of treatment. Sometimes this can be accomplished by surgery, but the propensity of cancers to invade adjacent tissue or to spread to distant sites by microscopic metastasis often limits its effectiveness. The effectiveness of chemotherapy is often limited by toxicity to other tissues in the body. Radiation can also cause damage to normal tissue.

One problem with current methods for treating the various forms of cancer is the inability to detect how well a particular type of therapy is working. For example, neoadjuvant chemotherapy in the treatment of breast cancer produces significant clinical benefit to patients (PR+CR rates>70%) (see, e.g., Early Breast Cancer Trialists' Collaborative Group: Polychemotherapy for early breast cancer: An overview of the randomized trials. Lancet 352, 930-942, 1998) and can be used to increase the numbers of patients eligible for a breast preservation procedure. Neoadjuvant chemotherapy has the benefit of allowing observation of chemoresponsiveness, and biological evaluation of the cancer both before and after chemotherapy administration.

The ability to observe an individual's tumor response is of increasing importance in this time of rapid development of new and more targeted drugs against cancer. It is essential to determine which new drugs will benefit patients. However, clinical benefit is an endpoint that can take years to accurately determine, and therefore surrogate endpoints for clinical benefit are often used in the evaluation of new drugs. Because of its positive association with disease free survival, pathologic complete response to neoadjuvant chemotherapy has become a widely utilized surrogate endpoint for breast cancer regimens. Pathologic complete response can be evaluated approximately 3-6 months after treatment begins, but it would be useful to have a surrogate for clinical benefit that would be evaluable at an even earlier time point.

As such, improved techniques for evaluating the effectiveness of a particular treatment are needed. In addition, improved techniques designed to evaluate the effectiveness of a particular treatment during the course of the treatment are needed and would provide for individualization of treatments. This would save patients from systemic toxicity from ineffective treatment and reduce costs to the health care system. Thus, further, improved techniques for evaluating candidate therapies are needed.

SUMMARY

The present invention provides systems and methods for monitoring tissue regions. In particular, the present invention provides systems and methods for detecting changes in tissue regions over a period of time. In some embodiments, the systems and methods of the present invention are used to evaluate the effectiveness of a particular treatment of a tissue region. In some embodiments, the systems and methods of the present invention provide a parametric response map approach for detecting and analyzing changes in tissue regions over a period of time to detect and monitor disease or tissue health and to monitor the impact of therapeutic interventions.

In some embodiments, the present invention utilizes imaging devices, control software, signal processing software, and display components that permit the collection of data, processing of data, and display of data according to any of the methods described herein. The systems may employ components configured together in a single device or may include multiple different devices in one or more locations. Where multiple devices are used, the device may be in wired or wireless communication with one another to permit the flow of data from device to device, as needed. In some embodiments, the present invention also provides user interfaces that display data generated by the novel methods described herein. For example, in some embodiments, multi-color tissue representations are provided that reveal changes in tissue over time. The changes may be represented any number of other ways as well. In some embodiments, the user interface is displayed on a computer monitor, a video monitor, a handheld device, or any other desired display device.

In some embodiments, the present invention provides systems and methods utilizing a parametric response map approach (PRM) for qualitative and/or quantitative analysis of hemodynamic alterations of a tissue following treatment with a medical intervention (e.g., a drug). Experiments conducted during the development of embodiments of the invention demonstrated the ability of these approaches to provide meaningful information at surprisingly early time points following initiation of an intervention. For example, the PRM method was applied to patients with grade III/IV glioma. Relative cerebral blood volume (rCBV) maps) were acquired pre-treatment and at 1 and 3 weeks following treatment. The standard approach of percent change in rCBV averaged over the tumor (% rCBV) and $PRM_{rCBV}$ were compared for prognostic effectiveness of patient outcome stratification based on overall survival. The $PRM_{rCBV}$ was found to predict patient response at 1 and 3 weeks from treatment initiation while the % rCBV was not. As such, the PRM imaging biomarker provides a method for analysis of perfusion data with greater prognostic value than current approaches.

In certain embodiments, the present invention provides methods for assessing the effectiveness of a treatment for a tissue region. The methods are not limited to particular manners of application. In some embodiments, the methods comprise obtaining a first set of parametric measurement data for a tissue region with an MRI device or other imaging device, administering a treatment to the tissue region, obtaining one or more subsequent sets of parametric measurement data for the tissue region with the MRI device or other imaging device, processing the sets of parametric measurement data with a parametric response map algorithm such that a parametric response map for the tissue region is generated, wherein the parametric response map characterizes spatially aligned tissue regions as having altered parametric measurement properties or unaltered parametric measurement properties, and assessing the effectiveness of the administered treatment based on parametric measurement properties. The methods are not limited to a particular form of treatment. Examples of a form of treatment include, but are not limited to, chemotherapy, radiation therapy, targeted therapy, cryotherapy, hyperthermia, proton beam therapy, ablation therapy, coagulation therapy, ultrasound therapy, antivascular therapy, and antiangiogenic therapy.

In certain embodiments, the present invention provides methods for determining the tumor burden for an individual comprising obtaining a first set of parametric measurement data for a large/whole body region with an MRI device or other imaging device, obtaining one or more subsequent sets of parametric measurement data for the large/whole region with the MRI device or other imaging device, processing the first and the one or more subsequent sets of parametric measurement data with a parametric response map algorithm such that a parametric response map for the large/whole region is generated, wherein the parametric response map images the multiple tumors within the individual, wherein the parametric response map characterizes the multiple tumors as having altered/unaltered parametric measurement properties; and determining changes in the tumor burden for the large/whole region.

In certain embodiments, the present invention provides methods for treating an individual diagnosed with cancer or assessing a therapy, comprising identifying a treatment designed to target a tissue region within the individual, wherein the tissue region comprises a tumor, obtaining a first set of parametric measurement data for the tissue region with an MRI device or other imaging device, administering the treatment to the individual, obtaining one or more subsequent sets of parametric measurement data for the tissue region with the MRI device or other imaging device, processing the sets of parametric measurement data with an parametric response map algorithm such that a parametric response map for the tissue region is generated, wherein the parametric response map characterizes the tissue region as having altered or unaltered parametric measurement properties, and assessing the effectiveness of the administered treatment. In some embodiments, the methods involve adapting the treatment, wherein the adapting comprises discontinuing or modifying the treatment if the parametric response map characterizes the treatment as ineffective, wherein the adapting comprises continuing the treatment if the parametric response map characterizes the treatment as effective.

In certain embodiments, the present invention provides methods for following the temporal evolution of an untreated tissue region for the purpose of detecting a status change within the tissue region, comprising obtaining a first set of parametric measurement data for a tissue region with an MRI device or other imaging device, obtaining one or more subsequent sets of parametric measurement data for the tissue region with the MRI device or other imaging device after obtaining the first set of parametric measurement data, processing the sets of parametric measurement data with a parametric response map algorithm such that a parametric response map for the tissue region is generated, wherein the parametric response map characterizes spatially aligned tissue regions as having altered parametric measurement properties or unaltered parametric measurement properties, and assessing the temporal evolution of an untreated tissue region based on parametric measurement properties. In some embodiments, the status change within the tissue region includes detecting a relapse, detecting the formation of a lesion, detecting changes in the growth pattern for the tissue region, detecting changes in the histological grade of the tissue region, detecting the spread of a tumor within the tissue region, detecting the presence of tumors within the region.

The methods are not limited to a particular tissue region. In some embodiments, the tissue region is a whole body. In some embodiments, the tissue region is a malignant tumor, a benign tumor, an abnormal growth, an inflamed region, a cancerous region, an infected region, a diseased region, an organ rejection, and/or one or more organs (e.g., lung, prostate, breast, colon, rectum, bladder, ovaries, skin, liver, spine, bone, pancreas, cervix, lymph, thyroid, adrenal gland, salivary gland, sebaceous gland, testis, thymus gland, penis, uterus, trachea, heart, spleen). In some embodiments, the tissue region is within a human being.

The imaging systems and methods are not limited to collecting and analyzing a particular type of perfusion parameter. In some embodiments, the systems and methods collect and analyze perfusion MRI parameters. In some embodiments, the perfusion MRI parameters include, but are not limited to, absolute blood volume (e.g., absolute cerebral blood volume), relative blood volume (e.g., relative cerebral blood volume ($PRM_{rCBV}$)), relative blood flow (e.g., relative cerebral blood flow ($PRM_{rCBF}$)), vascular permeability (e.g., AUC, leakage space, $PRM_K^{trans}$), extravascular leakage space ($PRM_{Ve}$), mean transit time data, and time to peak data. In some embodiments, the systems and methods collect and analyze perfusion CT parameters. In some embodiments, the systems and methods collect and analyze perfusion positron emission tomography (PET) parameters. In some embodiments, the systems and methods collect and analyze perfusion single photon emission computed tomography (SPECT) parameters. In some embodiments, the parametric measurement data is not apparent diffusion coefficient (ADC) data.

In some embodiments, the altered parametric measurement properties comprise increased parametric measurement properties and decreased parametric measurement properties. In some embodiments, the increased parametric measurement properties are displayed in a first color, decreased parametric measurement properties are displayed in a second color, and unaltered parametric measurement properties are displayed in a third color. In some embodiments, the increased parametric measurement properties are displayed in a first pattern, decreased parametric measurement properties are displayed in a second pattern, and unaltered parametric measurement properties are displayed in a third pattern. In some embodiments, the increased parametric measurement properties, decreased parametric measurement properties, and unaltered parametric measurement properties are displayed through a gradient of colors (e.g., a full spectrum of colors) (e.g., a gradient of gray scales).

In some embodiments, the treatment is assessed effective if the parametric response map characterizes a tissue region as comprising regions of increased parametric measurement properties, wherein the treatment is assessed ineffective if the parametric response map characterizes the tissue region as comprising regions of unchanged parametric measurement properties. In some embodiments, the treatment is assessed effective if the parametric response map characterizes the tissue region as comprising regions of decreased parametric measurement properties, wherein the treatment is assessed ineffective if the parametric response map characterizes the tissue region as comprising regions of unchanged parametric measurement properties. In some embodiments, the treatment is assessed effective if the parametric response map characterizes the tissue region as comprising regions of increased and decreased parametric measurement properties, wherein the treatment is assessed ineffective if the parametric response map characterizes the tissue region as comprising regions of unchanged parametric measurement properties.

The systems and methods of the invention provide prognostic information for analyzing patient samples. This information is provided in a short time frame (e.g., less than a month, 14 days, 10 days, 8 days, 7 days, . . . ). This is a capability not realized with prior existing technologies, providing physicians and researchers with significant new options for detecting and monitor diseases and disorders and the effectiveness of therapies against these diseases and disorders.

DETAILED DESCRIPTION

Figure 1:
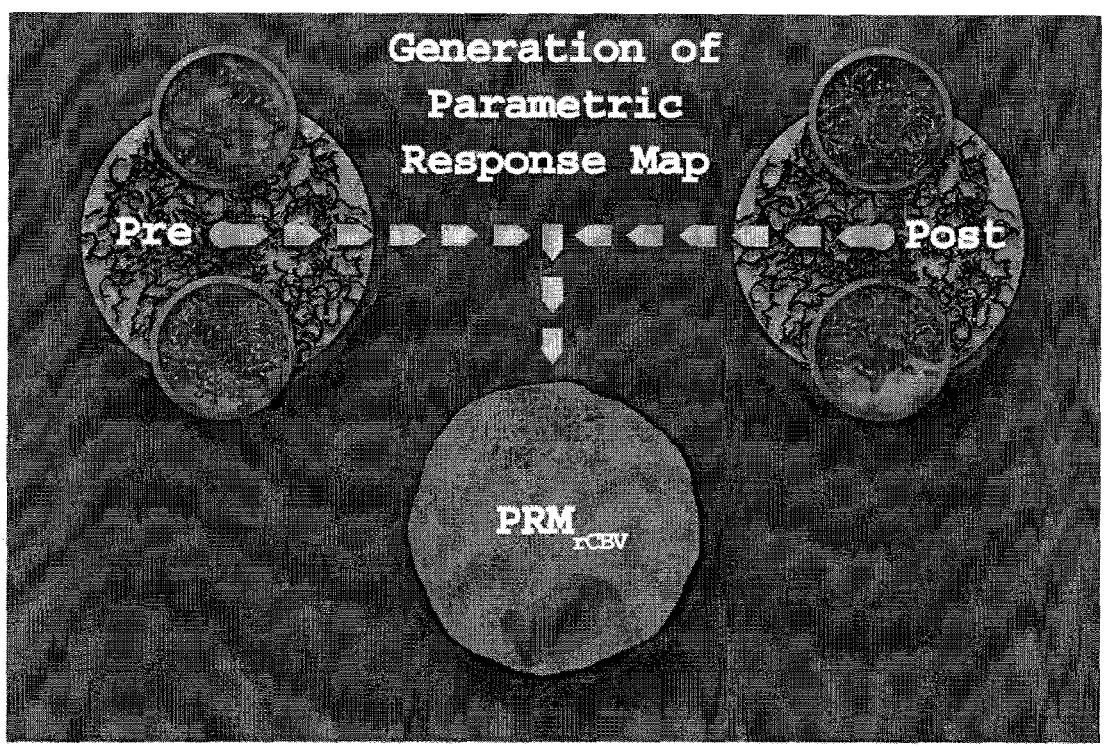
FIG. 1 shows generation of a functional parametric map. Schematic representation of tumor vasculature at pre- and post-treatment. Color-coding has been used to highlight regions of changed blood volume on $PRM_{rCBV}$ where red designates regions with increased blood volume as a result of increasing vessel number or size (red bordered insert); blue designates a decrease in blood volume from a loss or shrinkage in vessels (blue bordered insert); and green designates regions of unchanged blood.

The present invention provides systems and methods for monitoring tissue regions. The systems and methods of the present invention employ parametric response map approaches (PRM), using a number of different modalities (described herein as $PRM_x$), for assessing changes in tissue over time, including changes caused by medical interventions. In some embodiments, the systems and methods of the present invention are used to evaluate the effectiveness of a particular treatment of a tissue region. In some embodiments, the systems and methods of the present invention provide a parametric response map approach for detecting and analyzing changes in tissue regions over a period of time to detect and monitor disease or tissue health and to monitor the impact of therapeutic interventions.

The present invention is not limited to the monitoring of a particular tissue region. In some embodiments, the tissue region is within a living subject (e.g., dog, cat, human, gorilla, cow, sheep, rat, mouse, etc.). In some embodiments, the tissue region is within a living human being. In some embodiments, the tissue region is a diseased tissue region (e.g., a malignant tumor, a benign tumor, an abnormal growth, an inflamed region, a cancerous region, an infected region, an organ rejection). In some embodiments, the tissue region is a body region of the subject (e.g., lung, bone, heart, leg, foot, stomach, brain, neck, liver, breast). In some embodiments, the tissue region is the entire body of the subject.

The present invention is not limited to a particular type or manner of monitoring a tissue region. In some embodiments, the monitoring of a particular tissue region is accomplished through obtaining data measurements for the tissue region at different time points (e.g., two time points, three time points, five time points, fifty time points, etc.) (e.g., before treatment, during treatment, after treatment) and the characterization of changes within the tissue region between data measurements. The present invention is not limited to a particular method for characterizing changes within the tissue region between data measurements. In some embodiments, the characterization involves detecting one or more changes of a particular biological parameter within various regions within the tissue region. The present invention is not limited to detecting changes in a particular biological parameter within a tissue region. Examples of biological parameters within a tissue region that may be assessed for changes include, but are not limited to, changes in blood volume of the tissue region, changes in blood perfusion of the tissue region, changes in vascular leakage parameters of the tissue region, changes in density of the tissue region, changes in composition of the tissue region, changes in diffusion anisotropy-dependent parameters in the region, etc (see, also, e.g., Tofts, P. S. (1997) J Magn Reson Imaging 7, 91-101; Hylton, N. (2006) J Clin Oncol 24, 3293-3298 (2006); Tofts, P. S., et al. (1999) J Magn Reson Imaging 10, 223-232; Kiessling, F., et al., (2007) Curr Med Chem 14, 77-91). Functional imaging approaches complement, for example, anatomical MRI scans and are increasingly used in clinical practice for diagnosis and treatment response assessment (see, e.g., O'Connor, J. P., et al., Br J Cancer 96, 189-195 (2007); Zahra, M. A., et al., Lancet Oncol 8, 63-74 (2007); Cao, Y., et al. Int J Radiat Oncol Biol Phys 64, 876-885 (2006)). Dynamic contrast-enhanced (DCE) and dynamic susceptibility-weighted contrast (DSC) MRI methods provide information related to a variety of hemodynamic parameters including microvessel permeability-surface area product, blood volume, and blood flow (see, e.g., Ostergaard, L., et al., Magn Reson Med 36, 715-725 (1996); Rosen, et al., Magn Reson Med 14, 249-265 (1990); Brix, G., et al. Magn Reson Med 52, 420-429 (2004); Brix, G., et al. J Comput Assist Tomogr 15, 621-628 (1991); Hoffmann, U., Magn Reson Med 33, 506-514 (1995); Tofts, P. S.; J Magn Reson Imaging 7, 91-101 (1997); Degani, H., Nat Med 3, 780-782 (1997)). Several rudimentary analyses of the signal- or concentration-time curves following contrast agent administration have been described including slope of the curve, time to peak, maximum peak enhancement, wash out and area under the curve (see, e.g., Galbraith, S. M., et al. NMR Biomed 15, 132-142 (2002); Hylton, N. J Clin Oncol 24, 3293-3298 (2006); Thomas, A. L., et al. J Clin Oncol 23, 4162-4171 (2005); Xiong, H. Q., et al. Invest New Drugs 22, 459-466 (2004)). These descriptive parameters have been used in routine clinical applications primarily for tumor tissue characterization. Relatively complex pharmacokinetic modeling is required to derive physiological parameters, though these models tend to be based on simplifying assumptions and regimes where exchange of contrast material between the vascular space and interstitium is either flow limited, or permeability limited (see, e.g., Tofts, P. S., et al. J Magn Reson Imaging 10, 223-232 (1999); Eyal, E. & Degani, H. NMR Biomed (2007)). This requirement has led to the development of a diverse compilation of contrast agents for the purpose of increasing overall signal enhancement and blood pool localization as well as numerous mathematical models (see, e.g., Kiessling, F., Curr Med Chem 14, 77-91 (2007)). It has been suggested that validation and routine use of perfusion MRI as a biomarker of treatment response will require standardization of acquisition and quantification methods, with the latter being the more difficult due to the diverse number of methods (see, e.g., Hylton, N. J Clin Oncol 24, 3293-3298 (2006)). The lack of consensus for a standardized post-processing approach for analysis of perfusion MRI data is in part due to the need for a relatively large clinical data set to evaluate and compare the accuracy of different quantification methods used to compute pharmacokinetic parameters along with available clinical outcome measures (e.g., overall survival) as the gold standard.

The present invention is not limited to the collecting and analysis of a particular type of data for a tissue region. In some embodiments, the tissue region is imaged at different time points for purposes of characterizing the tissue region. In some embodiments, the imaging is used to determine physiological, morphological and/or anatomical changes within the tissue region. In some embodiments, the imaging is used to determine one or more blood perfusion values within the tissue region. The imaging systems and methods are not limited to collecting and analyzing a particular type of perfusion parameter. In some embodiments, the systems and methods collect and analyze perfusion MRI parameters. In some embodiments, the perfusion MRI parameters include, but are not limited to, relative cerebral blood volume ($PRM_{rCBV}$), vascular permeability ($PRM_K^{trans}$), and extravascular leakage space ($PRM_{Ve}$). In some embodiments, the systems and methods collect and analyze perfusion CT parameters. In some embodiments, the systems and methods collect and analyze perfusion positron emission tomography (PET) parameters. In some embodiments, the systems and methods collect and analyze perfusion single photon emission computed tomography (SPECT) parameters.

In experiments conducted during the course of development of embodiments for the present invention, the parametric response map ($PRM_x$) was utilized as a novel, voxel-wise image analysis approach for quantification of hemodynamic alterations following treatment. For example, the method was applied to patients with grade III/IV glioma. Relative cerebral blood volume (rCBV) maps were acquired pre-treatment and at 1 and 3 weeks following treatment. The standard approach of percent change in rCBV averaged over the tumor (% rCBV) and $PRM_{rCBV}$ were compared for prognostic effectiveness of patient outcome stratification based on overall survival. The $PRM_{rCBV}$ was found to predict patient treatment response at 1 and 3 weeks from treatment initiation. Indeed, the PRM imaging biomarker provided a standardized method for analysis of perfusion data with greater prognostic value than current approaches.

The present invention is not limited to a particular manner of implementing parametric response map ($PRM_x$) (where x is any type of parametric data) analysis within a tissue region. In some embodiments, the present invention provides algorithms configured to correlate perfusion MRI parameter measurements (e.g., relative cerebral blood volume ($PRM_{rCBV}$), vascular permeability ($PRM_K^{trans}$), and extravascular leakage space ($PRM_{Ve}$)) taken at different times. In some embodiments, an algorithm is provided in a system with an MRI device such that upon imaging of a particular tissue region with the MRI device, a PRM image is automatically generated. In some embodiments, the algorithm is configured to automatically generate a PRM for a particular tissue region. In some embodiments, a PRM for a particular tissue region distinguishes between regions within the tissue region with different measured parameters (e.g., blood perfusion, relative cerebral blood volume, vascular permeability, extravascular leakage space). In some embodiments, such distinguished changes are presented within a tissue region image on a display as color differences (e.g., red indicating increased blood perfusion, blue indicating decreased blood perfusion, green indicating unchanged blood perfusion) (e.g., varied color or other gradient schemes distinguishing between, for example, ultra-high blood perfusion alteration, moderately-high blood perfusion alteration, minimally-high blood perfusion alteration, and no blood perfusion alteration) (see, e.g., Examples I-IV, below).

In some embodiments, the systems and methods are used to quantify changes in tissue regions, where the existence of or degree of change is prognostic or otherwise indicative of disease state, response to therapy, or another desired tissue status criteria of interest. The systems and methods of the present invention provide an improvement over, for example, whole-tumor average methods. Indeed, $PRM_x$ retains spatio-regional alterations in perfusion parameter measurements (e.g., perfusion MRI parameter measurements) (e.g., cerebral blood volume values) following, for example, a treatment initiation. For example, FIG. 1 shows that a tumor environment may have three local hemodynamic outcomes throughout the course of therapy. An increase in, for example, rCBV above a specified threshold corresponds to a significant increase in the microvascular density or enlargement of blood vessel diameter (e.g., blood volume) within the tumor, in which case these voxels would be color coded, for example, red in the PRM analysis approach applied to rCBV ($PRM_{rCBV}$). Alternatively, treatment may result in a significant reduction in rCBV within the tumor in which case voxels within those regions would be coded, for example, blue. Voxels in regions which were relatively unaffected by therapy would be coded, for example, green. In some embodiments, the $PRM_{rCBV}$ analysis retains the spatial rCBV information as coded by color overlayed on anatomic images and also quantification of the total number of tumor voxels (on a percentage of total tumor volume or voxel number) which exhibited an increase (red: $V_I$), decrease (blue: $V_D$) or unchanged (green: $V_0$) rCBV values using scatter plot analysis.

In some embodiments, quantification of spatially altered perfusion parameter measurements is used as a prognostic imaging biomarker for early treatment response assessment. The present invention is not limited to a particular manner of using spatially altered perfusion parameter measurements as a prognostic imaging biomarker for early treatment response assessment. In some embodiments, spatially altered perfusion parameter measurements are used as a prognostic imaging biomarker for early treatment response assessment correlation with overall patient survival.

In some embodiments, the present invention provides methods of treating a diseased tissue region (e.g., a malignant tumor). In such embodiments, a diseased tissue region is administered a treatment directed toward the particular tissue region, and the treatment monitored over the course of the treatment with $PRM_x$. In some embodiments, a particular type of treatment is altered if the $PRM_x$ indicates that the tissue region is not responding to the treatment. Changes include, but are not limited to, changing medication, dosing, route of administration, frequency, and the like.

In some embodiments, the present invention provides methods for screening the effectiveness of types of treatment of diseased tissue regions (e.g., malignant tumors, benign tumors, etc.). In such embodiments, types of treatment (e.g., pharmaceutical treatment, radiation based treatment, chemotherapeutic treatment, radiation sensitizer treatment, gene therapy based treatment, cancer vaccine based treatment) designed to treat a particular tissue region are evaluated based upon the ability to effectively treat (e.g., reduce blood perfusion in a tumor; increase blood perfusion in a tumor; reduce the size of a tumor; increase/decrease vascular leakage parameters; increase/decrease the density of a tumor; increase/decrease the diffusion anisotropy-dependent parameters of a tumor) the tissue region as measured with $PRM_x$ at various time points. In some embodiments, treatments identified as effective in treating a tissue region as measured with $PRM_x$ may be used to treat similar types of diseased tissue regions in the same individual and/or in other individuals presenting similar diseased tissue regions.

In some embodiments, $PRM_x$ is used to characterize an individual's disease (e.g., provide an overall prognosis). For example, $PRM_x$ databases for similar tissue regions having similar disease patterns (e.g., liver tumors resulting from liver cancer) may be generated according to any number of variables (e.g., treatment response; blood perfusion change over a certain amount of time; overall treatment outcome; etc.). The $PRM_x$ database can be used to generate expected treatment plans based on expected treatment outcome for such a tissue region having such a disease. In some embodiments, a health care professional obtains a $PRM_x$ for a patient's tissue region during and/or after a course of treatment and compares the $PRM_x$ with one or more $PRM_x$ from similar tissue regions from similar types of patients or from the same patient. In some embodiments, such a comparison is used to fine tune a treatment plan based on the expected treatment outcome as identified in the $PRM_x$ database.

EXAMPLES

The following examples are offered to illustrate various embodiments of the invention, but should not be viewed as limiting the scope of the invention.

Example I

This example describes the materials and methods for Examples II and III.

Patients Patients with pathologically proven grade III/IV gliomas were enrolled on a protocol of intra-treatment MRI. Informed consent was obtained. Fourty-four patients were evaluated pre-therapy, one week and three weeks post-treatment initiation. Radiotherapy (RT) was delivered using 3D-conformal therapy or Intensity Modulated Radiation Therapy (IMRT) with 6 MV or greater photons. Standard techniques were utilized with a 2.0-2.5 cm margin on either the enhancing region on gadolinium-enhanced scans or the abnormal signal on $T_2$-weighted scans to 46-50 Gy with the central gross tumor treated to a final median dose of 70 Gy in 6-7 weeks (see, e.g., Chan, J. L., et al. J Clin Oncol 20, 1635-1642 (2002). Twenty-four, at week one, of these patients were treated on a phase 2 protocol of high-dose (>60 Gy) radiation therapy concurrent with temozolamide. Chemotherapy was delivered as dependent upon clinical circumstances.

MRI Scans MRI scans were performed one week prior to and one and three weeks after the start of radiation with follow-up scans every 2-3 months. All images were acquired on either a 1.5T MRI system (General Electric Medical Systems, Milwaukee, Wis.) (n=30 patients) or a 3T Philips Achieva system (Philips Medical Systems, Best, The Netherlands) (n=14 patients). For dynamic susceptibility contrast (DSC) imaging, 14 to 20 slices of dynamic $T_2$*-weighted images were acquired by a gradient-echo echo-planar imaging pulse sequence (TR=1.5 to 2 s, TE=50 to 60 ms, field of view 220×220 mm$^2$, matrix 128×128, flip angle 60°, and 4 to 6 mm thickness and 0 mm gap). Gadolinium-diethylenetriamine pentaacetic acid (Gd-DTPA) was injected intravenously with a dose of 0.05 to 0.1 ml/kg as a bolus using a power injector at a rate of 2 mL/s, followed immediately by 15 cc of saline flush at the same rate. Subsequently a Gd-enhanced $T_1$-weighted imaging was acquired. Cerebral blood volume (CBV) maps were generated from DSC $T_2$*-weighted images (see, e.g., Cao, Y., et al. Int J Radiat Oncol Biol Phys 64, 876-885 (2006)).

To assess differences in tumor blood volume during RT and between patients, CBV maps were normalized to CBV values within white matter regions contralateral to the tumor to generate the relative CBV (rCBV). For simplicity in notation, relative blood volume for both brain and tumor are denoted by "rCBV." The following guidelines were used to define the white matter regions of interest for normalization: (1) contralateral to tumor, (2) received <30 Gy accumulated dose, and (3) as large as possible but avoiding regions with susceptibility artifacts and partial volume averaging.

Image Analysis Pre- and post-treatment rCBV maps were co-registered to Gd-enhanced $T_1$-weighted images acquired before RT using an automated mutual information and simplex optimization module (see, e.g., Meyer, C. R., et al. Med Image Anal1, 195-206 (1997)). Following co-registration, brain tumors, manually contoured by a neuroradiologist, were defined within the enhancing regions of the tumor on the Gd-enhanced $T_1$-weighted images. Shrinkage or growth of the tumor during the time between scans may have occurred; therefore, only voxels that were present in both the pre-RT and post-RT tumor volumes were included.

The parametric response map of rCBV ($PRM_{rCBV}$) was determined by first calculating the difference between the rCBV ($\Delta$rCBV=Post rCBV−Pre rCBV) for each voxel within the tumor pre-RT and at weeks 1 or 3. Voxels yielding $\Delta$rCBV greater than a predetermined threshold set to 1.23, were designated red (e.g., $\Delta$rCBV>−1.23). Blue voxels represent volumes whose rCBV decreased by more than 1.23 (e.g., $\Delta$rCBV <−1.23) and the green voxels represent voxels within the tumor that were unchanged (e.g., absolute value of $\Delta$rCBV was ≤1.23). The volume fractions within the tumor determined from $PRM_{rCBV}$ were $V_I$, increasing rCBV, $V_D$, decreasing rCBV, and $V_0$, unchanged rCBV. The thresholds that designate a significant change in rCBV within a voxel were empirically calculated from seven different patients. Other thresholds may be used, as desired. For each patient, a volume of interest within the contralateral brain containing normal gray and white matter was used to acquire a range of rCBV pre and three weeks post-therapy. Combining the data from all seven patients, linear least squares regression analysis was performed on the pre- and post-treatment rCBV values. The 95% confidence intervals were then determined from the results of the linear least squares analysis. Subsequently to the $PRM_{rCBV}$ analysis, the percent difference of the mean rCBV (% rCBV=[$rCBV_{post-RT}$−$rCBV_{pre-RT}$]/$rCBV_{pre-RT}$) over the tumor volume was calculated and compared to $PRM_{rCBV}$ results.

Statistical Analysis A receiver operator characteristic (ROC) curve analysis was performed for correlation of the representative imaging parameters with patient survival one year from diagnosis across all thresholds. The area under the ROC curve (ROC_AUC) was obtained to distinguish which continuous variables ($V_I$, $V_D$ and % rCBV) were predictive measures of outcome. For parameters whose ROC_AUC was statistically significant, cutoffs were selected based on optimal values of sensitivity and specificity. Patient population was then stratified based on the ROC cutoffs. Kaplan-Meier survival curves and the log-rank test were used to characterize and compare the groups in terms of overall survival. All statistical computations were performed with a statistical software package (SPSS Software Products, Chicago, Ill.), and results were declared statistically significant at the two-sided 5% comparison-wise significance level (p<0.05).

Example II

Figure 2:
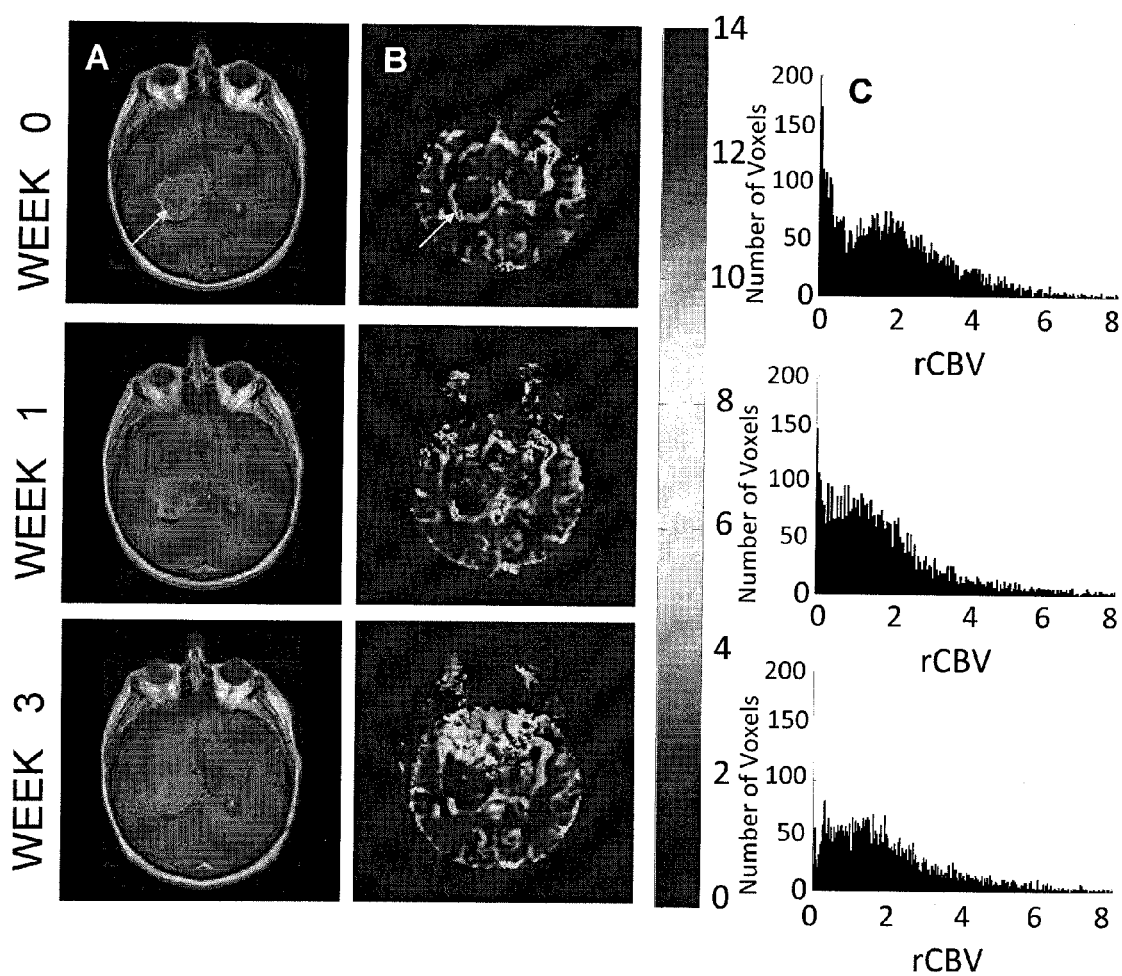
FIG. 2 shows a patient with a glioblastoma multiforme designated by $V_D$ from $PRM_{rCBV}$ stratification as a non-responder (survival time=2.9 months). (A) Gd-enhanced $T_1$-weighted MR image, (B) rCBV map with color scale for rCBV and (C) rCBV histogram of tumor, at 0, 1 and 3 weeks after initiation of radiotherapy. Location of tumor is designated by yellow arrow. Mean rCBV at 0, 1 and 3 weeks post-radiotherapy were 1.97, 1.95 and 2.13, respectively.

This example describes a comparison between $PRM_{rCBV}$ and rCBV analysis of perfusion MR images. Results of rCBV analysis from a representative patient diagnosed with a glioblastoma multiforme non-responsive to radiotherapy are presented in FIG. 2. The overall survival for this patient was 3 months from diagnosis. Signal hyperintensity in the Gd-enhanced $T_1$-weighted image was observed along the rim of the tumor at weeks 0, 1 and 3 (FIG. 2A), corresponding to disruption of the blood-brain-barrier. At week 1 of treatment, a slight attenuation in tumor rim enhancement was observed with a minor increase in enhancement within the core persisting through week 3. Tumor volume decreased slightly by 15% within the first week, and remained unchanged by the third week (week 0, 38 cc; week 1, 32 cc; week 3, 31 cc).

Prior to treatment (week 0) the tumor consisted primarily of a high blood volume rim with a low blood volume core which was attenuated at week 1 and 3 following treatment initiation as shown in rCBV maps (FIG. 2B). Following normalization by contralateral white matter, the distribution of rCBV values (FIG. 2C) within the tumor at week 0 ranged from 0 to 6 with a mean of 1.97. Significant numbers of voxels found to have rCBV's less than 1 were localized within the tumor core (FIG. 2B). At week 1 of therapy, mean rCBV decreased by <1% to 1.95 (FIG. 2C). As observed in FIG. 2B, a loss in rCBV along the tumor rim had occurred at week 1. The number of voxels with rCBV<1 had also decreased from pre-treatment values, as a result of increased rCBV within the tumor core. This had offset the observed loss in high rCBV along the tumor rim when calculating the mean. Increased rCBV within the tumor core, which is observed as increased Gd-enhancement in FIG. 2A, was more pronounced by week 3 as evidenced by a right-shift (FIG. 2C) of the mean rCBV (2.13), generating a mean rCBV value slightly higher than pre-treatment levels.

Figure 3:
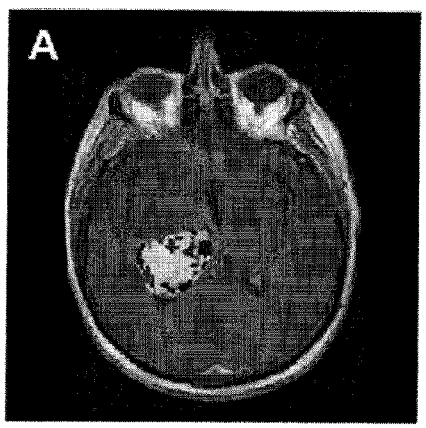
FIG. 3 shows $PRM_{rCBV}$ results from the same non-responding patient as shown in FIG. 2. (A) Representative slice of $PRM_{rCBV}$ color-coded ROI superimposed onto a Gd-enhanced $T_1$-weighted MR image 1 and 3 weeks post-radiotherapy. (B) Scatter plot showing the distribution of rCBV pre and post-radiotherapy for the entire 3-dimensional tumor volume. Relative volumes at Week 1 were: $V_D$ (blue dots designate voxels where rCBV decreased) of 19.9% and $V_I$ (red dots designate voxels where rCBV increased) of 17.2%. Relative volumes at Week 3 were: $V_D$ of 15.7% and $V_I$ of 20.4%.
Figure 3:
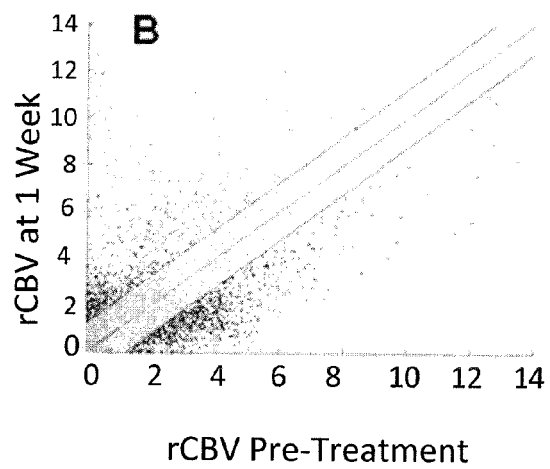
Figure 3:
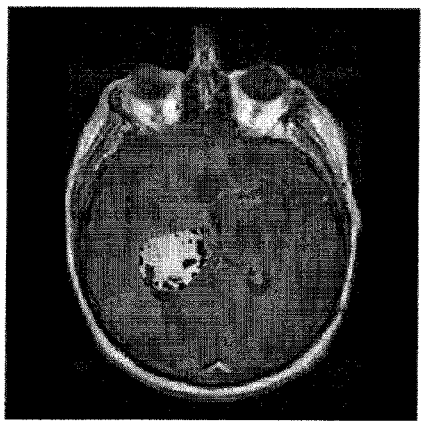
Figure 3:
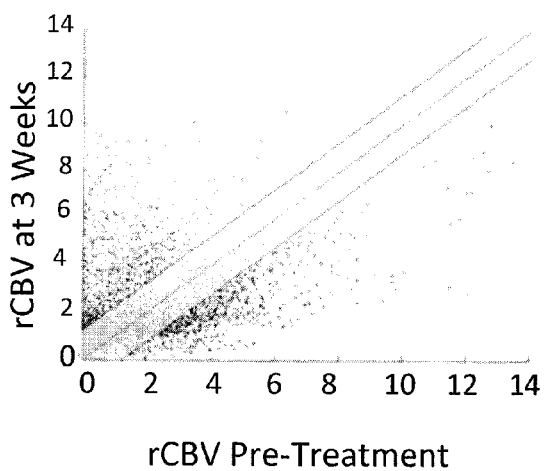

Presented in FIG. 3 is a $PRM_{rCBV}$ color overlay on the Gd-enhanced $T_1$-weighted image acquired at weeks 1 and 3 with the corresponding scatter plots quantitatively displaying the distribution of $PRM_{rCBV}$ voxels from the entire 3D tumor volume. The $PRM_{rCBV}$ analysis highlights regions where tumor blood volume change exceeded the ±1.23 thresholds. At weeks 1 and 3, significant changes in $PRM_{rCBV}$ voxels were observed near the periphery of the tumor (FIG. 3A). Scatter plot analysis (FIG. 3B) revealed that at weeks 1 and 3, $V_I$ was found to be 17.2% and 20.4% while $V_D$ was determined to be 20.0% and 15.7% of the total tumor volume, respectively.

Figure 4:
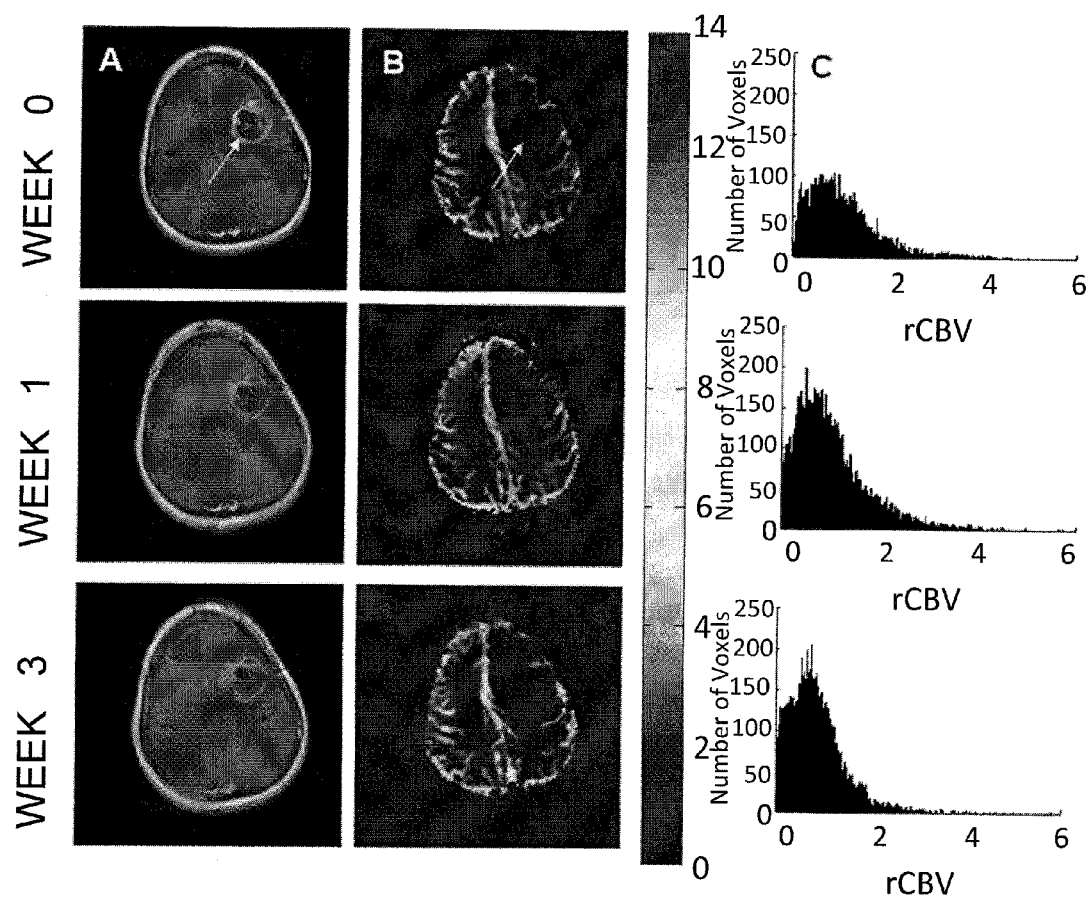
FIG. 4 shows a patient with a glioblastoma multiforme designated by $V_D$ from $PRM_{rCBV}$ stratification as a responder (survival time=20.4 months). (A) Gd-enhanced $T_1$-weighted MR image, (B) rCBV map with color scale for rCBV and (C) rCBV histogram of tumor, at 0, 1 and 3 weeks post-radiotherapy. Location of tumor is designated by yellow arrow. Mean rCBV at 0, 1 and 3 weeks post-radiotherapy were 1.02, 1.00 and 0.84, respectively.
Figure 5:
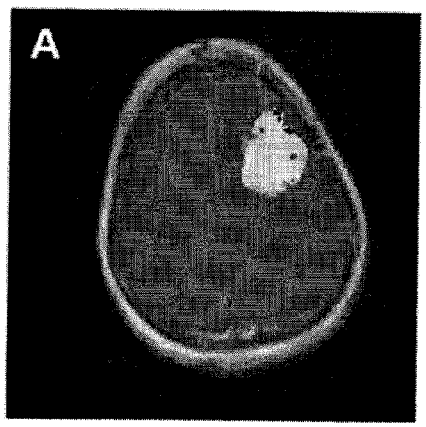
FIG. 5 shows $PRM_{rCBV}$ results from the same responding patient as shown in FIG. 4. (A) Representative slice of $PRM_{rCBV}$ color-coded ROI superimposed onto a Gd-enhanced T1-weighted MR image 1 and 3 weeks post-radiotherapy. (B) Scatter plot showing the distribution of rCBV pre and post-radiotherapy for the entire 3-dimensional tumor volume. Relative volumes at Week 1 were: $V_D$ (blue dots designate voxels where rCBV decreased) of 4.3% and $V_I$ (red dots designate voxels where rCBV increased) of 3.4%. Relative volumes at Week 3 were: $V_D$ of 4.6% and $V_I$ of 0.3%.
Figure 5:
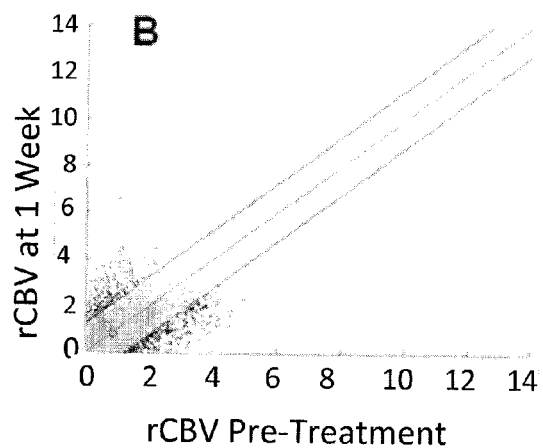
Figure 5:
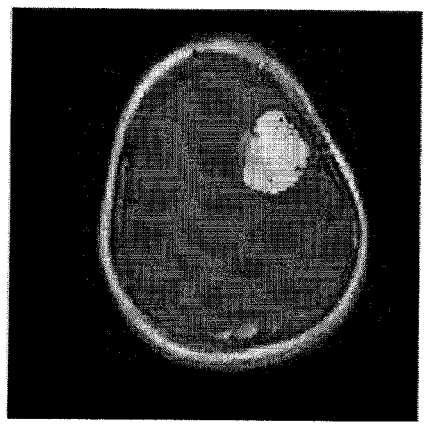
Figure 5:
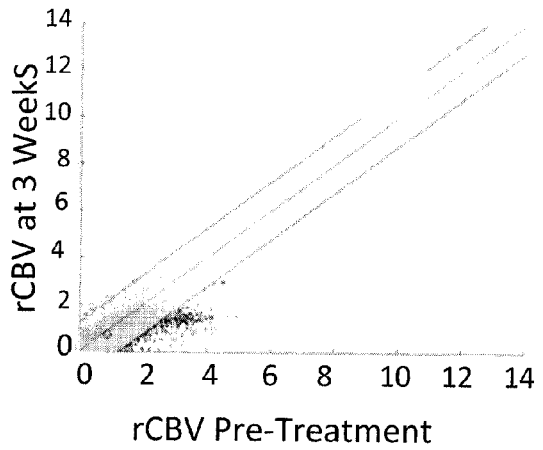

A representative patient diagnosed with a glioblastoma multiforme who responded to radiotherapy is presented in FIGS. 4 and 5. The overall survival of this patient was 20.4 months from diagnosis. Similar to the non-responsive patient, signal hyperintensity along the rim of the tumor was observed at week 0 and decreased slightly at weeks 1 and 3 in the Gd-enhanced $T_1$-weighted images (FIG. 4A). Negligible changes in contrast enhancement were observed in the tumor core. Over the initial course of treatment the tumor volume increased at week 1 from 40 cc to 50 cc and to 54 cc at week 3.

Regions of heterogeneity in the rCBV maps (FIG. 4B) were not as apparent as in the Gd-enhanced $T_1$-weighted images at weeks 0, 1 or 3. As observed in the rCBV histogram plots (FIG. 4C), the distribution of rCBV values ranged from 0 to 3. Mean rCBV values were found to be 1.02 at week 0, 1.00 at week 1 and 0.84 at week 3. The percent difference of the mean rCBV over the entire tumor at week 3 was approximately −18%.

$PRM_{rCBV}$ analysis of this patient showed negligible changes at 1 and 3 weeks of therapy (FIG. 5A). Shown in FIG. 5B are the corresponding scatter plots revealing $V_I$ and $V_D$ changed by 3.4% and 4.3%, respectively, at week 1. At week 3, $V_I$ and $V_D$ were 0.3% and 4.6% of the tumor volume, respectively. Clearly the $PRM_{rCBV}$ values in the therapeutically responsive patient were altered very little as compared with the non-responding patient.

Figure 6:
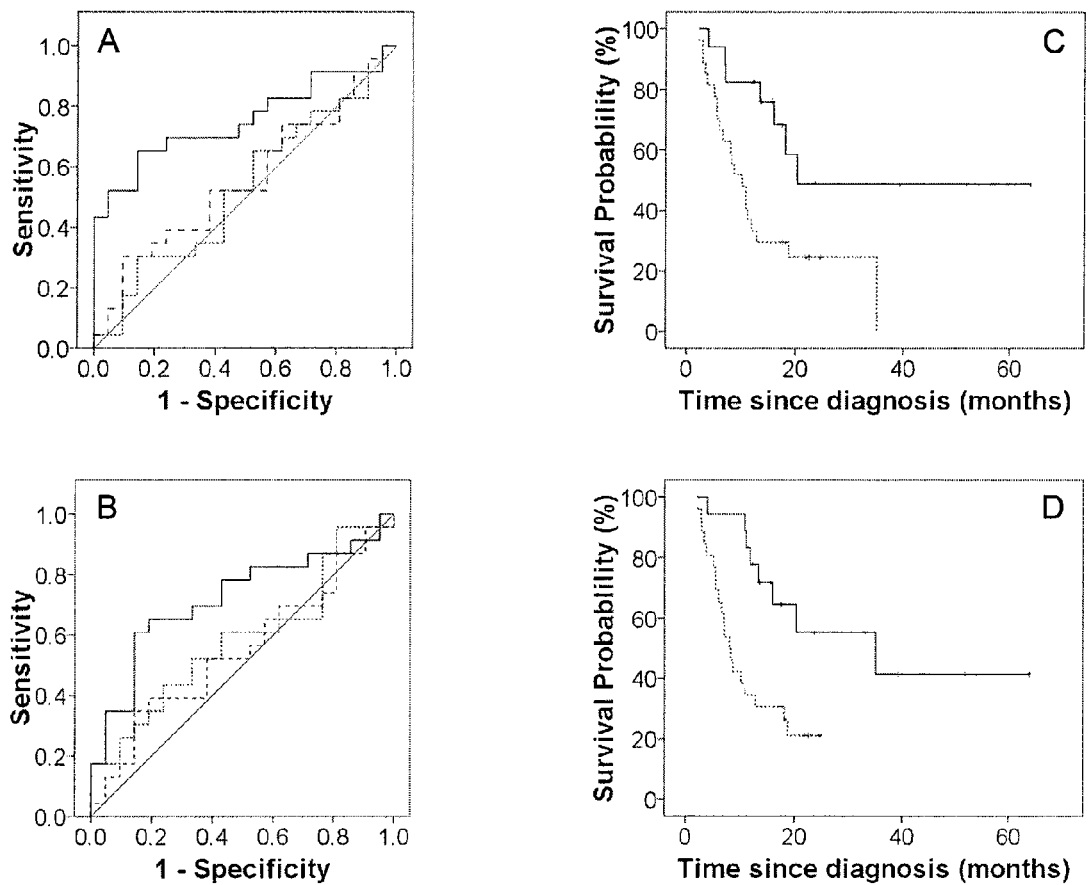
FIG. 6 shows receiver operating characteristic (ROC) curves for $V_D$ (solid line) and $V_I$ (small dashed line) from $PRM_{rCBV}$ and % rCBV (large dashed line) for weeks 1 (A) and 3 (B) post-treatment. Kaplan-Meier survival plots for overall survival are presented as a function of $V_D$ from $PRM_{rCBV}$ stratification at weeks 1 (C) and 3 (D) post-treatment. Solid line indicates $V_D \leq$ cutoff and dotted line indicates $V_D >$ cutoff (cutoff=6.4%; p=0.009).

As part of the imaging clinical trial design, overall survival data were obtained for this patient population for use as a clinical outcome correlate to evaluate the prognostic accuracy of each of the measured imaging biomarker parameters. Receiver operating characteristic (ROC) analysis was accomplished to select optimized thresholds for correlation analysis with overall survival from parameters whose area under the ROC curve (ROC_AUC) was found to be statistically significant. Of each of the three imaging biomarker parameters, $V_D$ was found to be significantly predictive of survival at one year with an AUC of 0.754 (p=0.004) resulting in a cutoff of 6.8% (FIG. 6A and Table 1). $V_I$ and % rCBV generated an ROC_AUC of 0.528 and 0.557, respectively, which are both equivalent to a random conjecture (Table 1). As shown in FIG. 6B and Table 1, $V_D$ at week 3 was again significantly predictive of survival at one year with an ROC_AUC of 0.710 (p=0.012) and a cutoff of 5.9%. $V_I$ and % rCBV were found to be non-predictive with an ROC_AUC of 0.584 and 0.549, respectively. For PRM to be suitable for clinical use the approach must be insensitive to cutoff value. Therefore, the mean value of the cutoffs from weeks 1 and 3 for $V_D$ (6.4%) were used for the overall survival analysis.

$PRM_{rCBV}$ measurements at weeks 1 and 3 exhibited a significant correlation with overall survival as shown in FIGS. 6C and D and Table 1. Patients whose $V_D$ was below or equal to the mean cutoff (6.4%) had a significantly longer median survival than patients whose $V_D$ was above the cutoff. Similar results for $V_D$ were observed at week 3.

TABLE 1

ROC and Survival Analysis Results

| Parameter | ROC_AUC | Median Survival (n) | p value |
|---|---|---|---|
| $V_D$ | 0.754 (p = 0.004) | 20.4/10.2 (17/27) | 0.009 |
| $V_I$ | 0.528 | — | — |
| % rCBV | 0.557 | — | — |
| $V_D$ | 0.720 (p = 0.012) | 35.1/8.1 (18/26) | 0.004 |
| $V_I$ | 0.584 | — | — |
| % rCBV | 0.549 | — | — |

Area under the ROC curve (ROC_AUC) and significant p values were generated from the ROC analysis. The mean of the optimal cutoffs at weeks 1 and 3, determined by ROC analysis, was used for the Kaplan-Meier analysis. Median survival and group populations (in parentheses) were presented for significant results (p values) generated from Kaplan-Meier and log-rank test. Median survival is split based on stratification of parameter: left value is ≤ cutoff; and right value is > cutoff. Statistical significance was assessed at p < 0.05.

Experiments were accomplished to demonstrate the PRM technique with various imaging parameters and tumor types and within a variety of host tissues.

Figure 7:
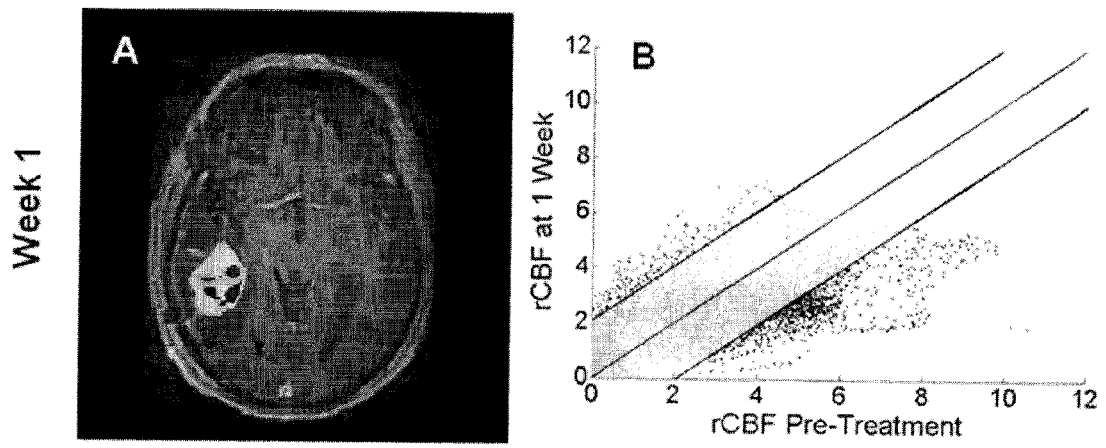
FIG. 7 shows a patient with a glioblastoma multiforme designated by $V_D$ from $PRM_{rCBF}$ stratification as a non-responder (survival time=6 months). Results from non-responding patient. (A) Representative slice of $PRM_{rCBF}$ color-coded ROI superimposed onto a Gd-enhanced $T_1$-weighted MR image 1 week post-radiotherapy. (B) Scatter plot showing the distribution of rCBF pre and post-radiotherapy for the entire 3-dimensional tumor volume. Relative volumes at Week 1 were: $V_D$ (blue dots designate voxels where rCBF decreased) of 14.1% and $V_I$ (red dots designate voxels where rCBF increased) of 3.5%.

The procedure for PRM using relative cerebral blood flow ($PRM_{rCBF}$) was analogous as described for $PRM_{rCBV}$ in Example I. Presented here are the results of the $PRM_{rCBF}$ analysis at one week. FIG. 7 shows a patient with a glioblastoma multiforme designated by $V_D$ from $PRM_{rCBF}$ stratification as a non-responder (survival time=6 months). FIG. 7A shows a representative slice of $PRM_{rCBF}$ color-coded ROI superimposed onto a Gd-enhanced $T_1$-weighted MR image 1 week post-radiotherapy. FIG. 7B shows a scatter plot showing the distribution of rCBF pre and post-radiotherapy for the entire 3-dimensional tumor volume. Relative volumes at week 1 were: $V_D$ (blue dots designate voxels where rCBF decreased) of 14.1% and $V_I$ (red dots designate voxels where rCBF increased) of 3.5%.

Figure 8:
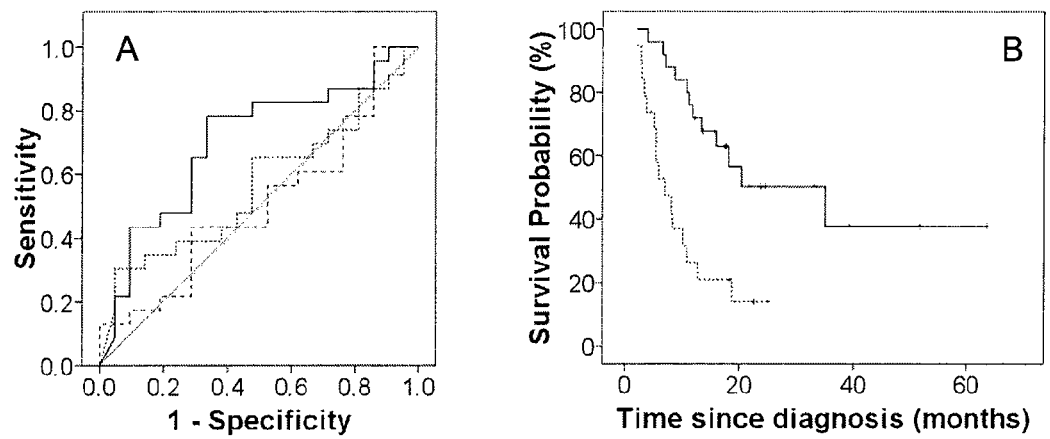
FIG. 8 shows (A) receiver operator characteristic curves for $V_D$ (solid line) and $V_I$ (small dashed line) from $PRM_{rCBF}$ and % rCBF (large dashed line) for weeks 1 post-treatment and (B) Kaplan-Meier survival plot for overall survival are presented as a function of $V_D$ from $PRM_{rCBF}$ stratification at weeks 1 post-treatment. Solid line indicates $V_D \leq$ cutoff and dotted line indicates $V_D >$ cutoff (cutoff=4.15%; p=0.001).

FIG. 8A shows receiver operator characteristic curves for $V_D$ (solid line) and $V_I$ (small dashed line) from $PRM_{rCBF}$ and % rCBF (large dashed line) for weeks 1 post-treatment. $V_D$ was found to be significantly predictive of survival at one year with an ROC_AUC of 0.704 (cutoff=4.15%, p=0.021). $V_f$ and % rCBF generated an ROC_AUC of 0.567 and 0.511, respectively. Kaplan-Meier survival plot, FIG. 8B, for overall survival is presented as a function of $V_D$ from $PRM_{rCBF}$ stratification at weeks 1 post-treatment. Solid line indicates $V_D \leq$ cutoff and dotted line indicates $V_D >$ cutoff (cutoff=4.15%; p=0.001).

Figure 9:
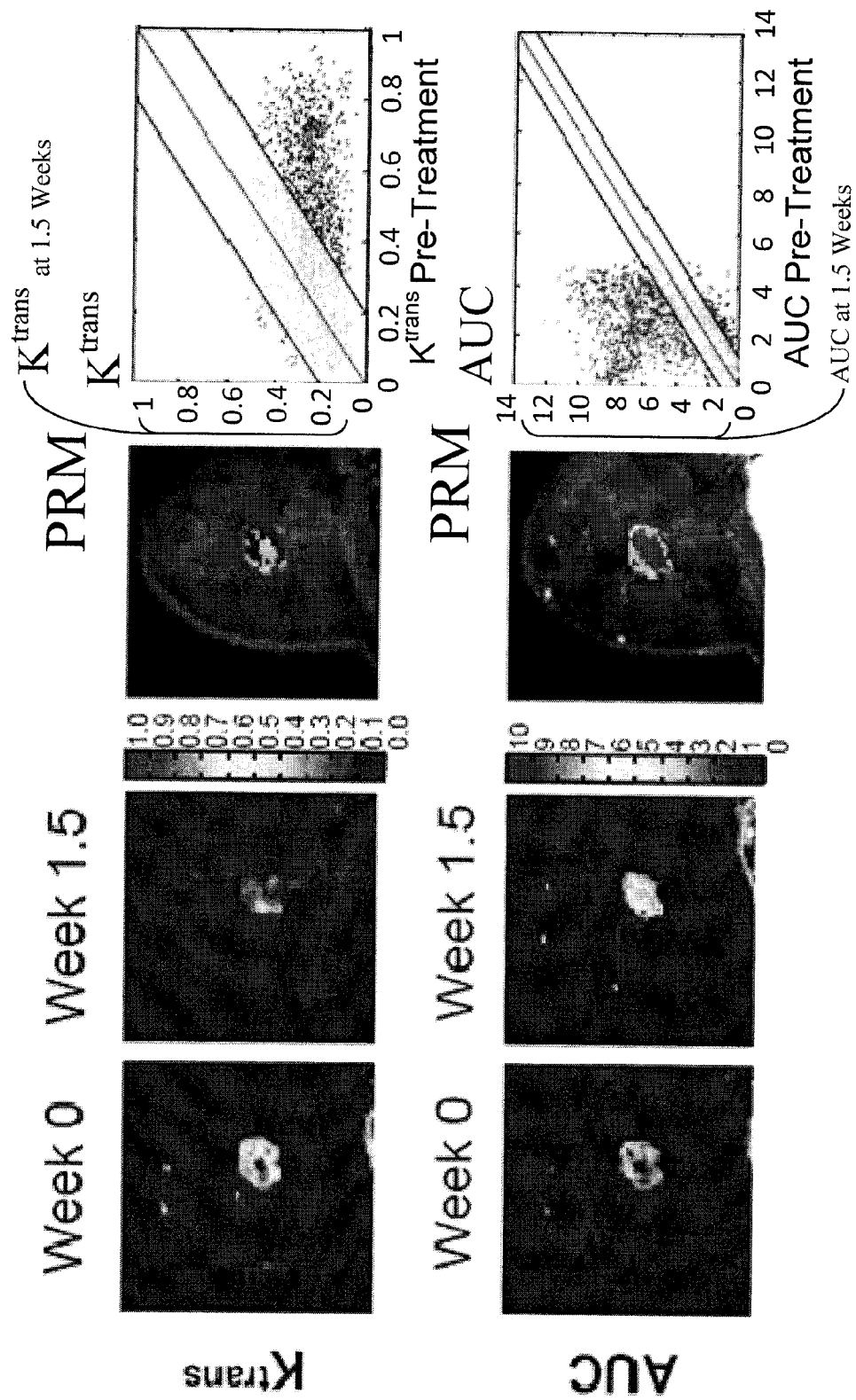
FIG. 9 shows mid-tumor axial images of the permeability constant ($K^{trans}$) and area under the curve (AUC) with corresponding PRM analyses for a breast cancer patient pre- (week 0) and post-treatment (week 1.5). PRM analysis includes PRM color-overlay and scatter plot. Thresholds, depicted as black lines in the scatter plots, were set to ±0.2 and ±1.2 for $K^{trans}$ and AUC, respectively.

The current demonstration is to highlight the versatility of the PRM approach. FIG. 9 shows mid-tumor axial images of the permeability constant ($K^{trans}$) and area under the curve (AUC) with corresponding PRM analyses, presented for a breast cancer patient pre- (week 0) and post-treatment (week 1.5). The PRM analysis includes PRM color-overlay and scatter plot. Thresholds, depicted as black lines in the scatter plots, were set to ±0.2 and ±1.2 for $K^{trans}$ and AUC, respectively.

Example III

This example describes a particular technique for generating a parametric response map ($PRM_x$) for quantifying changes in tissue regions over a period of time and/or in response to therapeutic interventions. The present invention is not limited to this particular technique.

First, images are acquired (e.g., MRI images; PET images; SPECT images; CT images) at different time points for a particular tissue region.

Second, the images obtained for the particular tissue region are spatially co-registered (see e.g., Lee et al., Neoplasia, 9(12):1003-1011 (2007); Meyer CR, et al., Med Image Anal. 1997; 1:195-206; and Kim, et al., Proc. Intl. Soc. Mag. Reson. Med. 8 (2000) 1765; each herein incorporated by reference in their entireties). Registration including rigid body, affine (linear) and/or warping image information from interval exams applied globally over the entire image sets and/or regionally over selected regions or areas.

Third, the error threshold is set. This step involves identification of the source of error. Acquisition error involves noise and artifacts. Co-Registration error involves misalignment of images. The procedure for setting the threshold involves drawing a region of interest around tissue with detailed contrast/heterogenous, good SNR/CNR, and anatomically and physiologically unchanged. The procedure also involves calculating a difference map ($X_{post}-X_{pre}$), and determining 95% confidence interval (e.g., plotting $X_{pre}$ vs. $X_{post}$, and performing a linear regression to calculate the confidence interval).

Fourth, Difference Maps ($X_{post}-X_{pre}$) following treatment are calculated.

Fifth, threshold voxel data is processed (e.g., Red: $\Delta X>$threshold; Green: $-$threshold$\leq \Delta X \leq$threshold; Blue: $\Delta X<-$threshold).

Sixth, data is represented (e.g., Scatter Plot $X_{pre}$ vs. $X_{post}$; shows distribution of X following treatment) (e.g., color overlay of PRM is superimposed on high SNR/contrast image; shows voxel-wise variation in X).

Example IV

Figure 10:
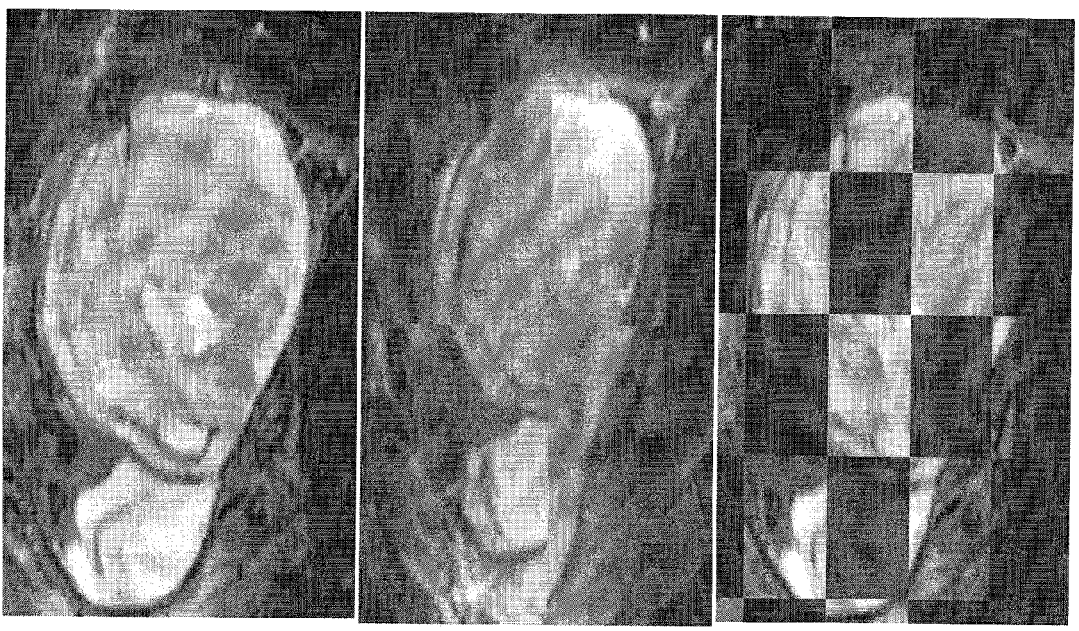
FIG. 10 shows co-registration of MRI studies in soft tissue sarcoma. A) Fat-suppressed T2-weighted image of pelvic liposarcoma prior to treatment. B) Overlay of post- and pretreatment scans based only on rigid body structures shows distortion of the tumor because of increases in volume over time. C) Checkerboard display of alternating images from pre- and 7-week post-treatment studies after post-processing using mutual information and warping shows precise registration of anatomic features within the tumor for subsequent PRM analysis.

This example describes whole tumor and PRM analysis of ADC and DCE-MRI data in soft tissue sarcoma. As proof-of-principle that PRM analysis enhances detection of therapy-induced changes in soft tissue sarcoma, diffusion and DCE-MRI was performed on a patient undergoing neoadjuvant chemotherapy with doxorubicin and ifosfamide. MRI studies after 1 and 7 weeks of therapy were co-registered with the pre-treatment examination. The use of warping registration methods accounted for the increase in tumor volume during neoadjuvant chemotherapy, as seen by precise alignment of pre- and 7-weeks post-treatment tumors on the checkerboard display (FIG. 10) (see, e.g., Meyer CR, et al., Med Image Anal. 1997; 1: 195-206; Kim, et al., Proc. Intl. Soc. Mag. Reson. Med. 8 (2000) 1765; Meyer, CR, (2006) Molecular Imaging 5(1):16-23; Kim, B, et al., (1997) NeuroImage 5(1): 31-40; Collignon, A, et al., (1995) Lecture Notes in Computer Science 905: 195-204; Viola, P, et al., (1995) Alignment by maximization of mutual information, in Proceedings of $5^{th}$ Int'l. Conf. on Computer Vision, MIT, IEEE Press 95CH35744: 16-23; Bookstein, FL (1989) IEEE Transactions on Pattern Analysis and Machine Intelligence 11(6): 567-585; Jacobs, M, et al., (1999) Medical Physics 26(8): 1568-1578; Pelizzari, CA, et al., (1987) J. Nucl. Med. 28(4): 683; Besl, P J, et al., (1992) IEEE Trans. Pattern Analysis and Machine Intelligence 14(2):239-256; Lazebnik, R, et al., IEEE Trans Med Imaging 22(5):653-660; Breen, M, et al., J Mag Res Imag 18:90-102; Wilson, D, et al., (2004) M Breen, R Lazebnik, S Nour, J Lewin (2004) Radiofrequency thermal ablation: 3D MR histology correlation for localization of cell death in MR lesion images, in Proceedings of Internat Symp Biomed Imaging, Arlington, Va.: 1537-1540; Zarow, C, et al., J Neuorsci Methods 139:209-215; Park, H, et al., M Piert, A Kahn, R Shah, H Hussain, J Siddiqui, C Meyer (2008) Registration methodology for histological sections and ex vivo imaging of human prostate, Academic Radiology (accepted for publication); each herein incorporated by reference in their entireties). Using these co-registered images, therapy-induced changes in ADC and Ktrans by whole-tumor mean values and PRM of spatially-localized changes in these parameters within the tumor was analyzed.

Figure 11:
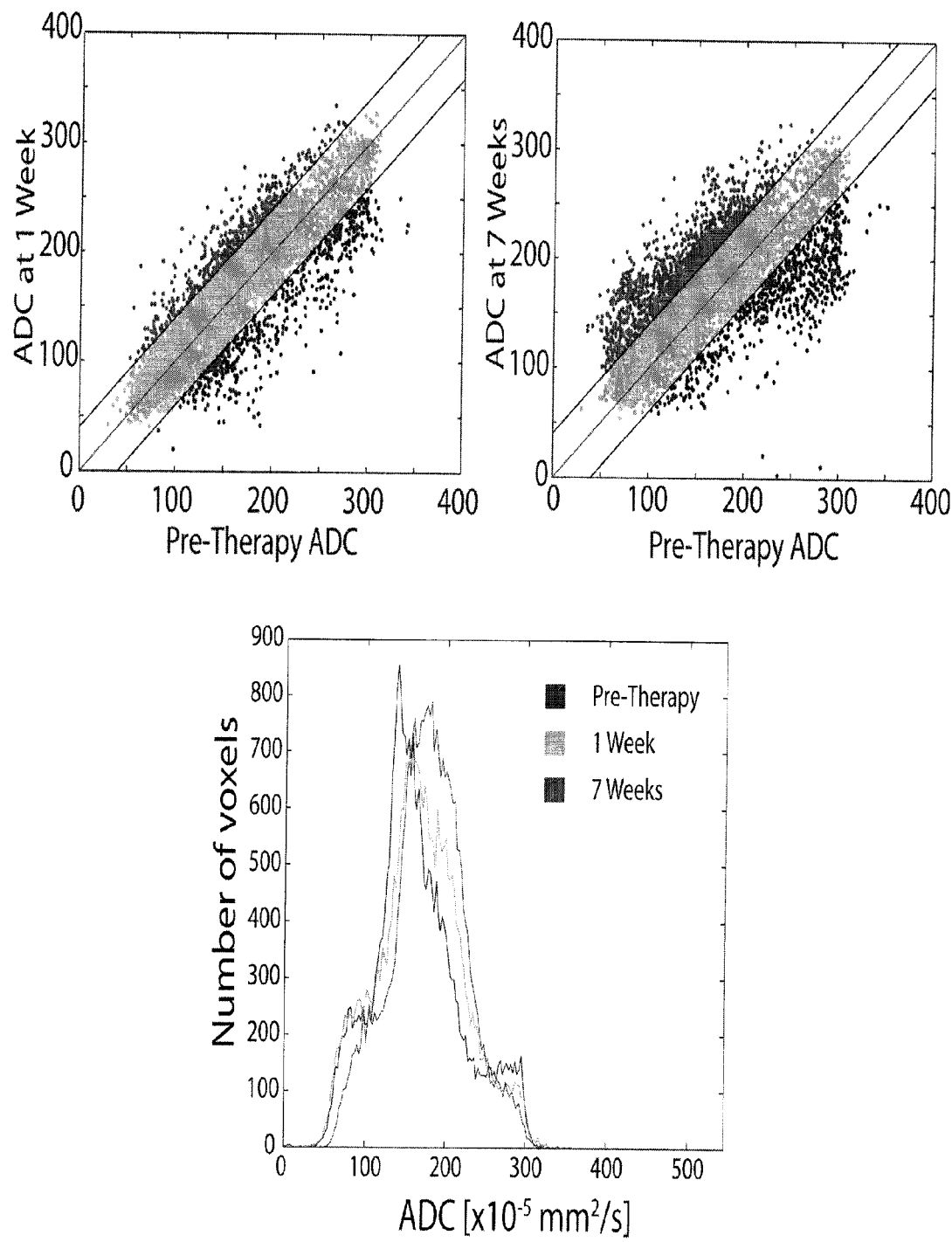
FIG. 11 shows whole tumor versus PRM analysis of ADC. (Left) Whole tumor analysis shows a minimal increase in mean ADC during neoadjuvant chemotherapy for pelvic liposarcoma with extensive overlap of all histograms (pretherapy, blue line; 1 week, green; 7 weeks, red). (Middle and Right) PRM scatter plots show notable changes in ADC (≈12% of all voxels) after 1 week of therapy (middle) that increase even more by 7 weeks (right).
Figure 12:
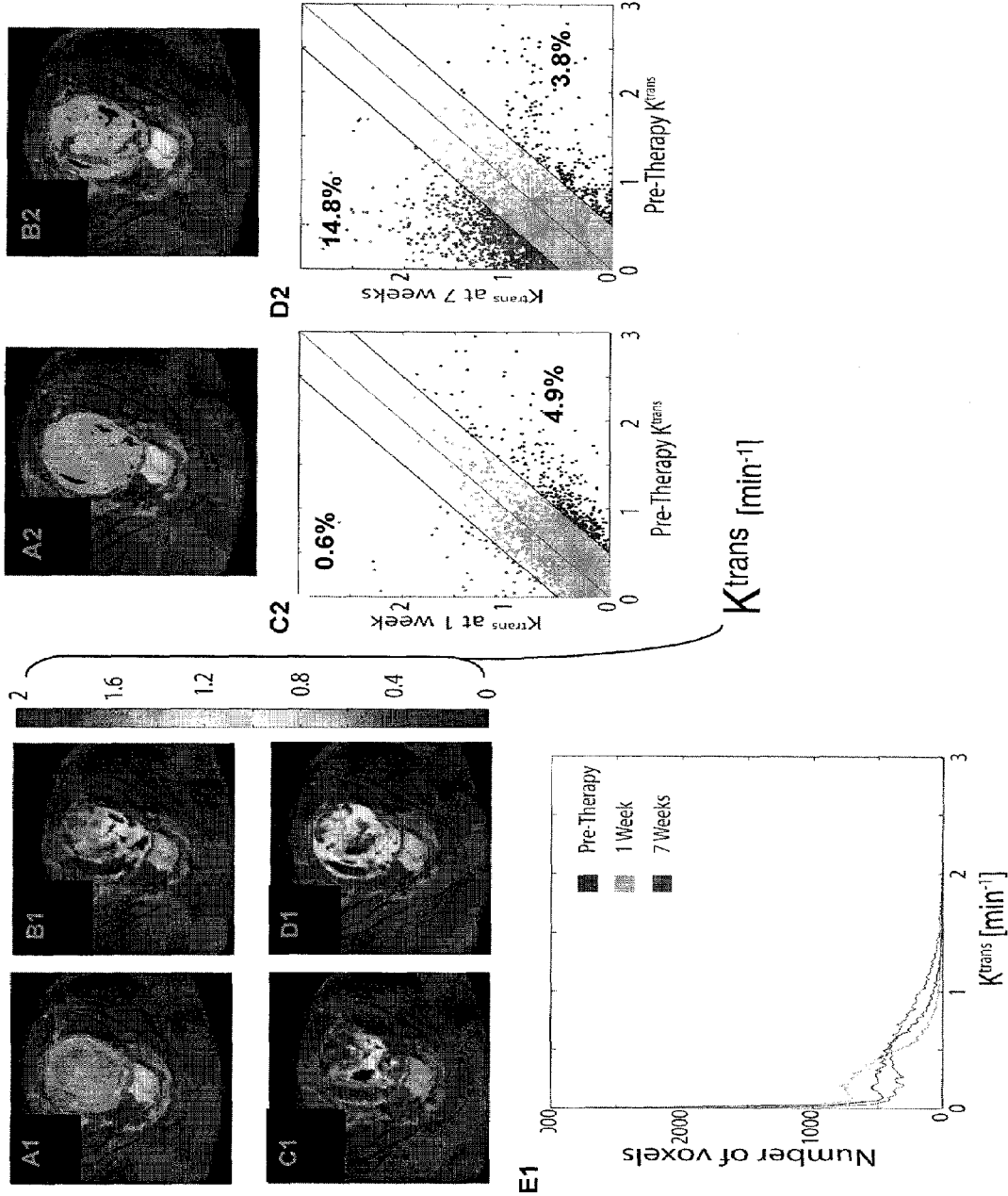
FIG. 12 shows whole tumor region of interest (A1) and pseudocolor display of Ktrans values from a representative image on pre-therapy (B1), 1 week (C1), and 7 week (D1) DCE-MRI studies. Whole tumor mean values for Ktrans (E1) lose spatial heterogeneity of changes within the tumor, resulting in small overall changes following therapy. PRM analysis of 1 week (A2, C2) and 7 week (B2, D2) studies utilizes spatial heterogeneity to substantially increase detection of therapy-induced changes in Ktrans over time.

Whole-tumor mean values for ADC increased only minimally after 1 and 7 weeks of therapy (<10% increase from baseline to 7 weeks). Histogram plots of whole tumor data were overlapping, further emphasizing the small dynamic range of standard whole-tumor analysis (FIG. 11). By comparison, PRM showed significant changes in ADC in 12% of all tumor voxels within 1 week of therapy, increasing to almost 30% of the entire tumor by 7 weeks. PRM also showed enhanced detection of chemotherapy-induced changes in Ktrans as compared with standard whole tumor analysis. Chemotherapy produced minimal effects on mean values for Ktrans within the entire tumor volume (FIG. 12). By incorporating spatial localization of Ktrans data and analyzing changes in these values on a voxel-by-voxel basis, PRM identified notably larger perturbations of Ktrans after 1 and 7 weeks of treatment. The patient had a favorable histologic response to chemotherapy. As such, PRM analysis of diffusion and DCE-MRI data enhances detection of therapy-induced changes in sarcomas relative to standard whole tumor analysis. In addition, PRM analysis permits identification of quantitative changes in MRI data that are early predictive biomarkers for response to neoadjuvant chemotherapy in bone and soft tissue sarcomas.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A computer-based method for generating a parametric response map comprising:
   a) obtaining a first set of parametric measurement data for a tissue region with an imaging device, the first set of parametric measurement data comprising a plurality of voxels; b) administering a treatment to the tissue region;
   c) obtaining one or more subsequent sets of parametric measurement data, each subsequent set of parametric measurement data comprising a plurality of voxels, and the subsequent sets of parametric measurement data being obtained with the imaging device or another imaging device;
   d) registering the one or more subsequent sets of parametric response data with the first set of parametric response data; and
   e) identifying, on a voxel-by-voxel basis, whether the voxels within the tissue region have increased, decreased, or unaltered parametric measurement properties, using a defined threshold, wherein each of the changes is determined by comparing voxels of the one or more subsequent sets of parametric measurement data to the voxels of one or more subsequent sets of parametric measurement data obtained previously or to the voxels of the first set of parametric measurement data.

2. The method of claim 1, wherein said treatment comprises a treatment selected from the group consisting of chemotherapy, radiation therapy, targeted therapy, cryotherapy, hyperthermia, proton beam therapy, ablation therapy, coagulation therapy, ultrasound therapy, antivascular therapy, and antiangiogenic therapy.

3. The method of claim 1, wherein said parametric measurement data comprise measures of vascular permeability data selected from the group consisting of K Trans, AUC, and leakage space.

4. The method of claim 1, wherein said parametric measurement data is selected from the group consisting of extravascular leakage space data, vascular permeability data, blood flow data, absolute blood volume data, relative blood volume data, mean transit time data, time to peak data, density data, composition data, diffusion data, and diffusion anisotropy data.

5. The method of claim 1, wherein said tissue region is selected from the group consisting of a malignant tumor, a benign tumor, an abnormal growth, an inflamed region, a cancerous region, an infected region, a diseased region, an organ rejection, and one or more organs selected from the group consisting of lung, prostate, breast, colon, rectum, bladder, ovaries, skin, liver, spine, bone, pancreas, cervix, lymph, thyroid, adrenal gland, salivary gland, sebaceous gland, testis, thymus gland, penis, uterus, trachea, heart, and spleen.

6. The method of claim 1, wherein at least one parametric response map is generated based on the processing that shows which voxels in the tissue region have increased, decreased, or unaltered parametric measurement properties.

7. The method of claim 6, wherein the parametric response map shows changes in parametric data as color changes.

8. The method of claim 1, wherein said tissue region is within a living human being.

9. The method of claim 1, wherein said processing with said registering occurs automatically after said obtaining of subsequent sets of parametric measurement data.

10. A device comprising a processor configured to process the sets of parametric measurement data with said method of claim 1 to generate the parametric response map.

11. The device of claim 10, comprising software that comprises said method to generate said parametric response map.

12. A system comprising the device of claim 10.

13. The system of claim 12, further comprising said imaging device.

14. The method of claim 1, wherein said identifying occurs automatically after said registering the one or more subsequent sets of parametric measurement data with the first set of parametric response data.

15. The method of claim 1, wherein a technique for the registration is selected from a group consisting of rigid body, affine (linear) and warping (non-linear) algorithms.

16. A computer-based method for generating a parametric response map that is used to optimize a therapeutic intervention, comprising:
   a) selecting a treatment designed to target a tissue region within an individual;
   b) obtaining a first set of parametric measurement data for said tissue region with an imaging device, the first set of parametric measurement data comprising a plurality of voxels;
   c) administering said treatment to said individual;
   d) obtaining one or more subsequent sets of parametric measurement data for said tissue region with said imaging device, each subsequent set of parametric measurement data comprising a plurality of voxels; and
   e) processing by means of a computer said sets of parametric measurement data with a parametric response algorithm such that the parametric response algorithm registers the one or more subsequent sets of parametric response data with the first set of parametric response data, and using a defined threshold, characterizes on a voxel-by-voxel basis said tissue region as having altered or unaltered parametric measurement properties, wherein each of the changes is determined by comparing voxels of the one or more subsequent sets of parametric measurement data to the voxels of one or more subsequent sets of parametric measurement data obtained previously or to the voxels of the first set of parametric measurement data.

17. The method of claim 16, wherein said parametric measurement data is selected from the group consisting of extravascular leakage space data, vascular permeability data, blood flow data, absolute blood volume data, relative blood volume data, mean transit time data, time to peak data, density data, composition data, diffusion data, and diffusion anisotropy data.

18. The method of claim 16, wherein said parametric measurement data comprise vascular permeability data.

19. The method of claim 16, wherein said parametric measurement data comprise extravascular leakage space data.

* * * * *